(12) United States Patent
Koch et al.

(10) Patent No.: US 11,846,624 B2
(45) Date of Patent: *Dec. 19, 2023

(54) IN-GROUND SENSOR SYSTEMS WITH MODULAR SENSORS AND WIRELESS CONNECTIVITY COMPONENTS

(71) Applicant: Climate LLC, Saint Louis, MO (US)

(72) Inventors: Justin Koch, Morton, IL (US); Michael H. Malone, Grand Rapids, MI (US); Phil David Baurer, West, TX (US); Nalini Gupta, Lafayette, CA (US); Calden Nathaniel Carroll Stimpson, Alameda, CA (US); Andreas Markus Wenzel, Seattle, WA (US); Jordan Kusiek, Beaverton, OR (US); Michael Gall, Saint Charles, MO (US); Jeffrey Lawrence Kohne, Kirkwood, MO (US); Eric L. Borrowman, Saint Peters, MO (US)

(73) Assignee: CLIMATE LLC, Saint Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/750,096

(22) Filed: May 20, 2022

(65) Prior Publication Data
US 2022/0283137 A1 Sep. 8, 2022

Related U.S. Application Data

(63) Continuation of application No. 16/660,402, filed on Oct. 22, 2019, now Pat. No. 11,346,832.
(Continued)

(51) Int. Cl.
*G01N 33/24* (2006.01)
*H04W 76/10* (2018.01)
(Continued)

(52) U.S. Cl.
CPC ......... *G01N 33/246* (2013.01); *A01B 79/005* (2013.01); *A01G 25/167* (2013.01);
(Continued)

(58) Field of Classification Search
CPC ................ G01N 33/24; G01N 33/246; G01N 2033/245; A01G 25/167; H04W 4/80; H04W 76/10; G01W 1/14; A01B 79/005
See application file for complete search history.

(56) References Cited

U.S. PATENT DOCUMENTS

2016/0187266 A1 6/2016 Annan et al.
2016/0223511 A1* 8/2016 Koshnick ............. A01C 21/007
(Continued)

OTHER PUBLICATIONS

Current Claims in application No. PCT/US19/57464, dated Jan. 2020.
(Continued)

*Primary Examiner* — Tuan H Nguyen
(74) *Attorney, Agent, or Firm* — Harness, Dickey & Pierce, P.L.C.

(57) ABSTRACT

In an embodiment, an integrated sensor system with modular sensors and wireless connectivity components for monitoring properties of field soil is described. In an embodiment, an integrated sensor system comprises one or more sensors that are configured to determine one or more measures of at least one property of soil. The integrated sensor system also includes one or more processing units that are configured to receive, from the sensors, the measures of at least one property of soil and calculate soil property data based on the measures. The system further includes a transmitter that is configured to receive the soil property data from the processing units, establish a communications connection with at least one computer device, and automatically transmit the soil property data to the at least one computer device via the communications connection. In an embodi-
(Continued)

ment, the communications connection is a wireless connection established between the transmitter and a smart hub or a LoRA-enabled device. In an embodiment, the computer sensors, the processors, and the transmitter are installed inside a portable probe.

18 Claims, 14 Drawing Sheets

Related U.S. Application Data

(60) Provisional application No. 62/750,129, filed on Oct. 24, 2018.

(51) Int. Cl.
*H04W 4/80* (2018.01)
*A01G 25/16* (2006.01)
*A01B 79/00* (2006.01)
*G01W 1/14* (2006.01)
*H04W 84/14* (2009.01)

(52) U.S. Cl.
CPC ............... *G01W 1/14* (2013.01); *H04W 4/80* (2018.02); *H04W 76/10* (2018.02); *G01N 2033/245* (2013.01); *H04W 84/14* (2013.01)

(56) References Cited

U.S. PATENT DOCUMENTS

| | | |
|---|---|---|
| 2017/0034986 A1 | 2/2017 | Koch et al. |
| 2017/0316124 A1 | 11/2017 | Lee |
| 2018/0259674 A1 | 9/2018 | Hu et al. |
| 2018/0279536 A1 | 10/2018 | Bindhammer |
| 2019/0101505 A1* | 4/2019 | Liu ......................... G01N 1/08 |

OTHER PUBLICATIONS

Koch et al., U.S. Office Action dated Jul. 14, 2021, directed to U.S. Appl. No. 16/660,402; 15 pages.
Koch et al., U.S. Office Action dated Oct. 29, 2021, directed U.S. Appl. No. 16/660,402; 16 pages.
The International Searching Authority, Search Report in application No. PCT/US19/57464, dated Jan. 17, 2020, 17 pages.

* cited by examiner

Fig. 2
(a)
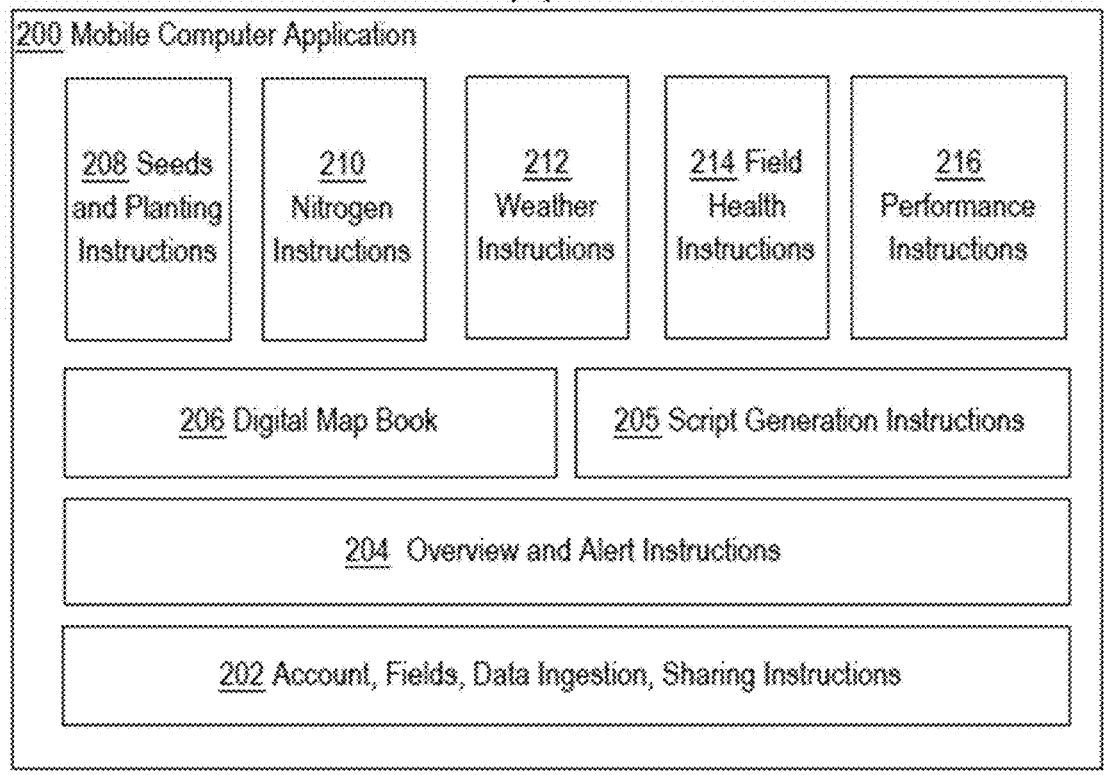
(b)
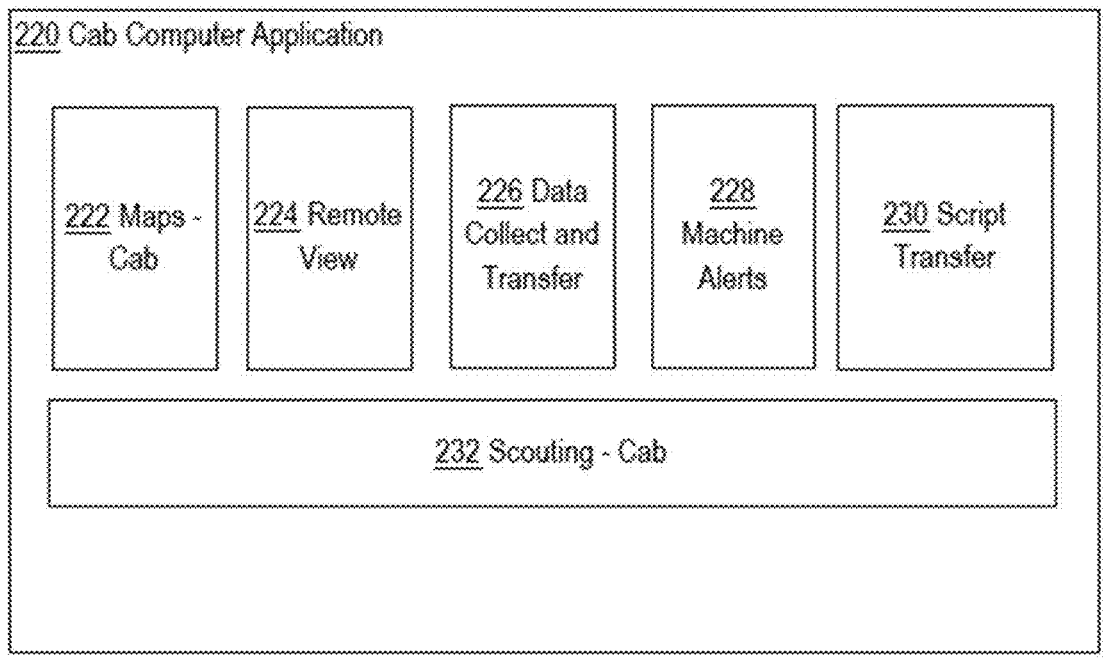

Fig. 6

IN-GROUND SENSOR SYSTEMS WITH MODULAR SENSORS AND WIRELESS CONNECTIVITY COMPONENTS

CROSS-REFERENCE TO RELATED APPLICATIONS

This application is a continuation of U.S. application Ser. No. 16/660,402, filed on Oct. 22, 2019, which claims the priority of U.S. Provisional Application No. 62/750,129, filed Oct. 24, 2018, the entire contents of each of which are incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright or rights whatsoever. © 2015-2019 The Climate Corporation.

FIELD OF THE DISCLOSURE

One technical field of the present disclosure is field soil measurements in agriculture including sensors and processing units to calculate soil property data for an agricultural field, and data communications transmitters to wirelessly transmit the soil property data to computer devices.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section. Further, it should not be assumed that any of the approaches described in this section are well-understood, routine, or conventional merely by virtue of their inclusion in this section.

Crop growers and agronomists monitor amounts of nutrients in soil and use the nutrient information to improve agricultural practices for the soil. The monitoring process is, however, difficult because nutrient amounts in soil vary from one location to another. Furthermore, the amounts may vary with the sampling time, environmental conditions, and soil physical characteristics. The monitoring process also may be difficult because collecting the soil samples and sending them to laboratories is labor-intensive, and because receiving the results from laboratories takes several weeks.

Furthermore, the monitoring process may be inefficient because results received from the laboratories may be inaccurate. Since soil properties such as temperature, moisture, and nitrate fluctuate over time, infrequently collected soil samples rarely capture changes in the soil properties correctly. Thus, relying on results received from laboratories makes understanding and quantifying the changes quite challenging.

SUMMARY

The appended claims may serve as a summary of the disclosure.

BRIEF DESCRIPTION OF THE DRAWINGS

In the drawings:

FIG. 2 depicts two views of an example logical organization of sets of instructions in main memory when an example mobile application is loaded for execution.

FIG. 6 depicts an example embodiment of a spreadsheet view for data entry.

DETAILED DESCRIPTION

Figure 1:
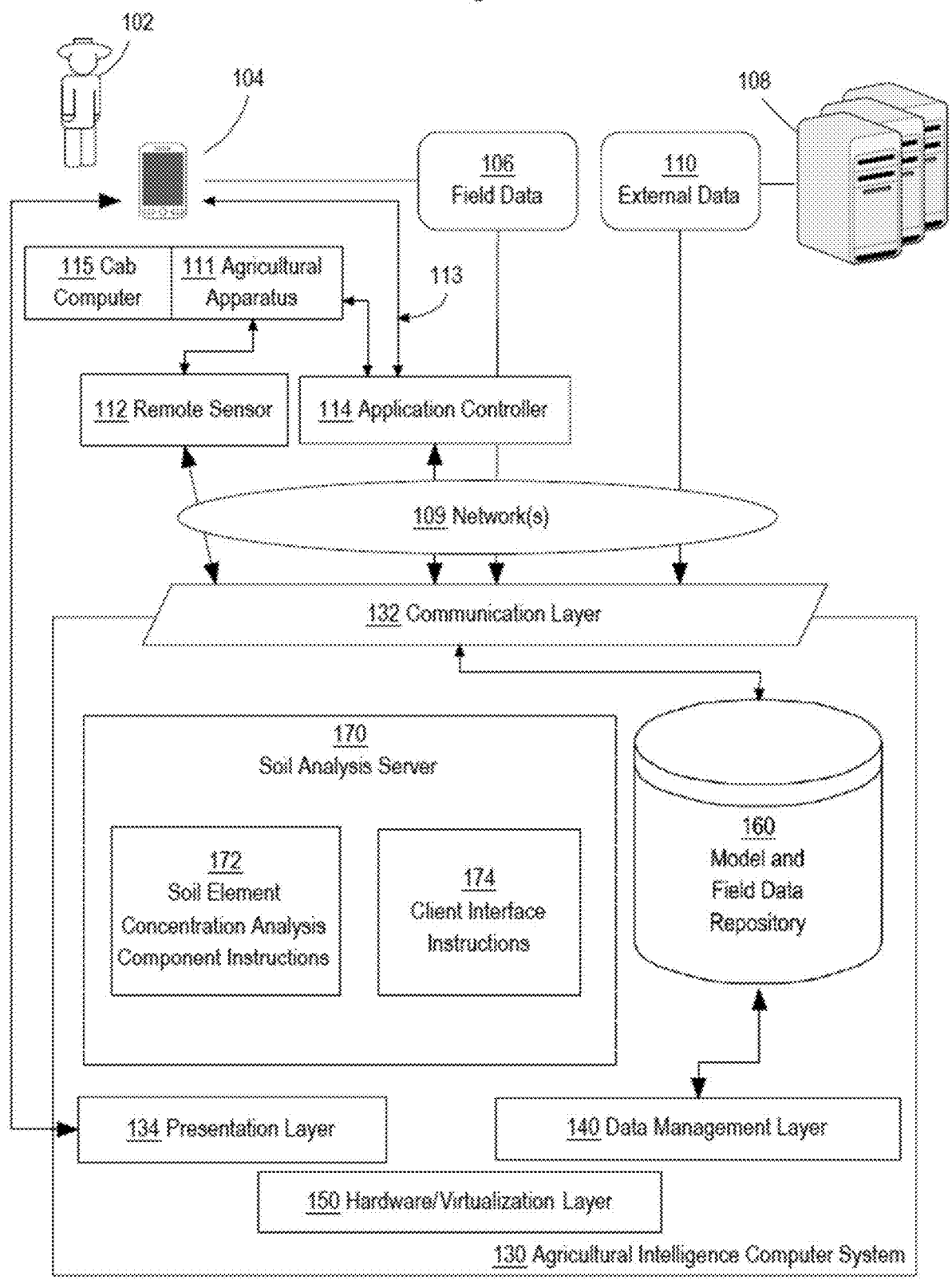
FIG. 1 depicts an example computer system that is configured to perform the functions described herein, shown in a field environment with other apparatus with which the system may interoperate.

In the following description, for the purposes of explanation, numerous specific details are set forth in order to provide a thorough understanding of the present disclosure. It will be apparent, however, that embodiments may be practiced without these specific details. In other instances, well-known structures and devices are shown in block diagram form in order to avoid unnecessarily obscuring the present disclosure. Embodiments are disclosed in sections according to the following outline:

1. GENERAL OVERVIEW
2. EXAMPLE AGRICULTURAL INTELLIGENCE COMPUTER SYSTEM
   2.1. STRUCTURAL OVERVIEW
   2.2. APPLICATION PROGRAM OVERVIEW
   2.3. DATA INGEST TO THE COMPUTER SYSTEM
   2.4. PROCESS OVERVIEW—AGRONOMIC MODEL TRAINING
   2.5. SOIL ANALYSIS
   2.6. IMPLEMENTATION EXAMPLE—HARDWARE OVERVIEW

3. IN-GROUND SENSOR SYSTEMS WITH MODULAR SENSORS AND WIRELESS CONNECTIVITY COMPONENTS
    3.1. SYSTEM OVERVIEW
    3.2. PROCESS OVERVIEW
4. EXAMPLE IMPLEMENTATIONS
    4.1. HANDHELD INTEGRATED SENSOR SYSTEMS
    4.2. BLADE-BASED INTEGRATED SENSOR SYSTEMS
5. EXTENSIONS AND ALTERNATIVES
6. IMPROVEMENTS PROVIDED BY CERTAIN EMBODIMENTS

1. General Overview

In one embodiment, an in-ground, integrated sensor system with modular sensors and communications connectivity components is described. The integrated sensor system may be used to calculate soil property data of soil properties in a field, and to transmit the soil property data to storage systems and computer devices. The system may be installed in the field and may be configured to measure the soil properties on-demand, according to a time schedule, and throughout a prolonged period of time. The integrated sensor system may be configured to transmit the soil property data to other devices via wireless communications connections established between the system and the devices. The versatility and convenience of the integrated system allows overcoming the shortcomings of conventional systems because the integrated system does not require sending physical soil samples to laboratories or awaiting receiving the soil property data from the laboratories.

In an embodiment, an integrated sensor system comprises one or more sensors, one or more processing units, and one or more communications devices. The sensors, processing units, and communications devices may be enclosed or sealed in a probe, or a container, which may protect the sensors, processors, and devices from dust, moisture, and other elements. The probe may be inserted into a cavity created in soil to allow the sensors measure soil properties as soon as the sensors are in contact with the soil. Examples of the soil properties may include nitrate concentrations, nitrite concentrations, ammonium concentrations, ammonia concentrations, sulfate concentrations, sulfite concentrations, iron concentrations, micronutrient concentrations, chloride concentrations, phosphorus concentrations, chlorine concentrations, pH levels, moisture levels, temperature, soil bulk density, or precipitation levels.

An integrated sensor system may be implemented in many types of portable devices, such as handheld devices, in-ground blades, or other devices that may be inserted into soil. The system may be powered up by conventional batteries and/or solar panels. Once the system is inserted into a cavity in the soil, adjusted in the soil to a desired depth, and powered up, the system may start measuring the soil properties.

To determine soil property data for soil, the integrated sensor system may use one or more sensors that are configured to measure soil properties in the soil. Examples of sensors may include capacitive moisture sensors, time-domain reflectometry moisture sensors, temperature sensors, and nitrate sensors. Each of the sensors may provide the measures to one or more processing units, and the processing units may use the received measures to calculate the soil property data. The soil property data may indicate, for example, a nitrate concentration level, a chloride concentration level, a phosphorus concentration level, a chlorine concentration level, a pH level, a moisture level, temperature, and/or a precipitation level.

An integrated sensor system may include additional devices, such as one or more imaging sensors, one or more anemometers, and one or more rainfall sensors. An imaging sensor may be also equipped with a digital camera or a video camera that is not lodged in a cavity in the ground, and that is configured to capture images of the scenery that the sensor can detect in its field of view. The anemometer may be used to, for example, measure the wind at the location where the integrated sensor system is installed.

The soil property data, and the additional data if such is provided, may be transmitted from the integrated sensor system to other devices. To transmit the data, the integrated sensor system may use one or more electronic data transmitters or transceivers that may be installed in the integrated system. Each transmitter may comprise an electronic device that is configured to establish a communications connection with another device and transmit data to that device, but it cannot receive data from another device. Each transceiver may comprise an electronic device that is configured to not only establish a communications connection with another device and transmit data to that device, but also to receive electronic data from devices. Hence, a transceiver is a device that provides functionalities of both a transmitter and a receiver. A communications connection established by a transmitter or a transceiver of an integrated sensor system may be any type of communications connection, including a wireless communications connection established in compliance with, for example, the Bluetooth communications protocol, or a radio-frequency ("RF") wireless communications protocol. In some embodiments, the transmitter or the transceiver may use wired communications connections of local area networks or wide area networks.

Upon establishing a communications connection with another device, the transmitter, or the transceiver, of the integrated system may transmit to the device the soil property data and additional data if such is available. This may include transmitting the soil property data to a storage device for storing and further processing. Examples of storage devices may include cloud-based storage systems, data servers, and data repository servers.

The soil property data may be transmitted to user devices, such as laptops, personal computers, mobile devices, tablets, smartphones, and the like. Upon receiving the soil property data, the user devices may be used to generate graphical representations of the data, display the graphical representations of the data on display devices, use the data to update agricultural data repositories, and/or transmit the data to computer-based controllers to control agricultural equipment.

In an embodiment, an integrated sensor system is assigned a universally unique identifier ("UUID"). The UUID may be used to identify a type and a location of the integrated sensor system. The UUID may be stored in one of the sensors or a memory unit included in the integrated sensor system or may be printed on a physical medium attached to the integrated sensor system. For example, the UUID may be encoded in a quick response (QR) code, and the QR code may be printed on a laminated label which may be affixed on a top portion of the integrated system. The UUID information may be included in soil property data that the integrated sensor system transmits to computer devices. A UUID may be determined by inspecting data that is received from the integrated system. For example, upon receiving the soil property data from the integrated system, the received data may be parsed, and an UUID may be extracted from the parsed data. Based on the extracted UUID, a type and a location of the integrated system may be determined. The UUID information may be used to, for example, associate the received soil property data with the location that corresponds to the UUID of the integrated system. The UUID information may also be used to associate the sensor with manufacturing or calibration data that is used to process the raw data into a calibrated soil property measurement. The association between the soil property data and the location of the integrated system may be stored in a data repository maintained for the field.

The process of associating soil property data with locations may be repeated each time soil property data is received from any of multiple integrated systems installed throughout a field. The associations may be stored in a data repository and may be used to generate graphical representations of the associations and displayed on display devices. The graphical representations may depict, for example, concentration levels of nitrate, chlorine, pH, phosphorus, or other matter throughout the field, and may be used to generate improved agricultural and irrigation practices for the field.

The ability to perform the content analysis of soil using an integrated sensor system with modular sensors and wireless connectivity components provides convenience and versatility. For example, a crop grower may use a plurality of integrated sensor systems installed throughout the field to determine concentration levels of nitrate at various location within the field and may do so as frequently as needed to monitor the rapidly changing levels of nitrate throughout the field. Based on the monitoring, the grower may modify fertilization prescriptions for the field as frequently as needed. For example, the grower may use soil property data received from the integrated systems to determine optimal schedules for cultivating the field, appropriate amounts of fertilizer for the filed, and appropriate timetables for applying fertilizers to the field.

Integrated sensor systems with modular sensors and wireless connectivity components may be used by agronomical researchers and developers working in technological centers. The researchers may use the provided soil property data to develop new seed varieties, enhance fertilization techniques, and develop enhancements to irrigation technologies. The received soil property data may be also used to monitor the fields with a high vulnerability to chemical pollution, and to develop strategies and environment-aware practices for handling the soil nutrient losses.

The soil property data may be provided to computer-based controllers that control agricultural equipment operating in the field. For example, the information that includes both nitrate concentration information for the soil and an UUID of the integrated sensor system that determined the nitrate concentration in the soil may be used by a computer-based controller installed on a fertilizer machine to either increase or decrease the amount of fertilizer as the fertilizer machine applies the fertilizer to the soil.

2. Example Agricultural Intelligence Computer System 2.1 Structural Overview

FIG. 1 illustrates an example computer system that is configured to perform the functions described herein, shown in a field environment with other apparatus with which the system may interoperate. In one embodiment, a user 102 owns, operates or possesses a field manager computing device 104 in a field location or associated with a field location such as a field intended for agricultural activities or a management location for one or more agricultural fields. The field manager computer device 104 is programmed or configured to provide field data 106 to an agricultural intelligence computer system 130 via one or more networks 109.

Examples of field data 106 include (a) identification data (for example, acreage, field name, field identifiers, geographic identifiers, boundary identifiers, crop identifiers, and any other suitable data that may be used to identify farm land, such as a common land unit (CLU), lot and block number, a parcel number, geographic coordinates and boundaries, Farm Serial Number (FSN), farm number, tract number, field number, section, township, and/or range), (b) harvest data (for example, crop type, crop variety, crop rotation, whether the crop is grown organically, harvest date, Actual Production History (APH), expected yield, yield, crop price, crop revenue, grain moisture, tillage practice, and previous growing season information), (c) soil data (for example, type, composition, pH, organic matter (OM), cation exchange capacity (CEC)), (d) planting data (for example, planting date, seed(s) type, relative maturity (RM) of planted seeds, seed population), (e) fertilizer data (for example, nutrient type (Nitrogen, Phosphorus, Potassium), application type, application date, amount, source, method), (f) chemical application data (for example, pesticide, herbicide, fungicide, other substance or mixture of substances intended for use as a plant regulator, defoliant, or desiccant, application date, amount, source, method), (g) irrigation data (for example, application date, amount, source, method), (h) weather data (for example, precipitation, rainfall rate, predicted rainfall, water runoff rate region, temperature, wind, forecast, pressure, visibility, clouds, heat index, dew point, humidity, snow depth, air quality, sunrise, sunset), (i) imagery data (for example, imagery and light spectrum information from an agricultural apparatus sensor, camera, computer, smartphone, tablet, unmanned aerial vehicle, planes or satellite), (j) scouting observations (photos, videos, free form notes, voice recordings, voice transcriptions, weather conditions (temperature, precipitation (current and over time), soil moisture, crop growth stage, wind velocity, relative humidity, dew point, black layer)), and (k) soil, seed, crop phenology, pest and disease reporting, and predictions sources and databases.

A data server computer 108 is communicatively coupled to agricultural intelligence computer system 130 and is programmed or configured to send external data 110 to agricultural intelligence computer system 130 via the network(s) 109. The external data server computer 108 may be owned or operated by the same legal person or entity as the agricultural intelligence computer system 130, or by a different person or entity such as a government agency, non-governmental organization (NGO), and/or a private data service provider. Examples of external data include weather data, imagery data, soil data, or statistical data relating to crop yields, among others. External data 110 may consist of the same type of information as field data 106. In some embodiments, the external data 110 is provided by an external data server 108 owned by the same entity that owns and/or operates the agricultural intelligence computer system 130. For example, the agricultural intelligence computer system 130 may include a data server focused exclusively on a type of data that might otherwise be obtained from third party sources, such as weather data. In some embodiments, an external data server 108 may actually be incorporated within the system 130.

An agricultural apparatus 111 may have one or more remote sensors 112 fixed thereon, which sensors are communicatively coupled either directly or indirectly via agricultural apparatus 111 to the agricultural intelligence computer system 130 and are programmed or configured to send sensor data to agricultural intelligence computer system 130. Examples of agricultural apparatus 111 include tractors, combines, harvesters, planters, trucks, fertilizer equipment, aerial vehicles including unmanned aerial vehicles, and any other item of physical machinery or hardware, typically mobile machinery, and which may be used in tasks associated with agriculture. In some embodiments, a single unit of apparatus 111 may comprise a plurality of sensors 112 that are coupled locally in a network on the apparatus; controller area network (CAN) is example of such a network that can be installed in combines, harvesters, sprayers, and cultivators. Application controller 114 is communicatively coupled to agricultural intelligence computer system 130 via the network(s) 109 and is programmed or configured to receive one or more scripts that are used to control an operating parameter of an agricultural vehicle or implement from the agricultural intelligence computer system 130. For instance, a controller area network (CAN) bus interface may be used to enable communications from the agricultural intelligence computer system 130 to the agricultural apparatus 111, such as how the CLIMATE FIELDVIEW DRIVE, available from The Climate Corporation, San Francisco, California, is used. Sensor data may consist of the same type of information as field data 106. In some embodiments, remote sensors 112 may not be fixed to an agricultural apparatus 111 but may be remotely located in the field and may communicate with network 109.

The apparatus 111 may comprise a cab computer 115 that is programmed with a cab application, which may comprise a version or variant of the mobile application for device 104 that is further described in other sections herein. In an embodiment, cab computer 115 comprises a compact computer, often a tablet-sized computer or smartphone, with a graphical screen display, such as a color display, that is mounted within an operator's cab of the apparatus 111. Cab computer 115 may implement some or all of the operations and functions that are described further herein for the mobile computer device 104.

The network(s) 109 broadly represent any combination of one or more data communication networks including local area networks, wide area networks, internetworks or internets, using any of wireline or wireless links, including terrestrial or satellite links. The network(s) may be implemented by any medium or mechanism that provides for the exchange of data between the various elements of FIG. 1. The various elements of FIG. 1 may also have direct (wired or wireless) communications links. The sensors 112, controller 114, external data server computer 108, and other elements of the system each comprise an interface compatible with the network(s) 109 and are programmed or configured to use standardized protocols for communication across the networks such as TCP/IP, Bluetooth, CAN protocol and higher-layer protocols such as HTTP, TLS, and the like.

Agricultural intelligence computer system 130 is programmed or configured to receive field data 106 from field manager computing device 104, external data 110 from external data server computer 108, and sensor data from remote sensor 112. Agricultural intelligence computer system 130 may be further configured to host, use or execute one or more computer programs, other software elements, digitally programmed logic such as FPGAs or ASICs, or any combination thereof to perform translation and storage of data values, construction of digital models of one or more crops on one or more fields, generation of recommendations and notifications, and generation and sending of scripts to application controller 114, in the manner described further in other sections of this disclosure.

In an embodiment, agricultural intelligence computer system 130 is programmed with or comprises a communication layer 132, presentation layer 134, data management layer 140, hardware/virtualization layer 150, and model and field data repository 160. "Layer," in this context, refers to any combination of electronic digital interface circuits, microcontrollers, firmware such as drivers, and/or computer programs or other software elements.

Communication layer 132 may be programmed or configured to perform input/output interfacing functions including sending requests to field manager computing device 104, external data server computer 108, and remote sensor 112 for field data, external data, and sensor data respectively. Communication layer 132 may be programmed or configured to send the received data to model and field data repository 160 to be stored as field data 106.

Presentation layer 134 may be programmed or configured to generate a graphical user interface (GUI) to be displayed on field manager computing device 104, cab computer 115 or other computers that are coupled to the system 130 through the network 109. The GUI may comprise controls for inputting data to be sent to agricultural intelligence computer system 130, generating requests for models and/or recommendations, and/or displaying recommendations, notifications, models, and other field data.

Data management layer 140 may be programmed or configured to manage read operations and write operations involving the repository 160 and other functional elements of the system, including queries and result sets communicated between the functional elements of the system and the repository. Examples of data management layer 140 include JDBC, SQL server interface code, and/or HADOOP interface code, among others. Repository 160 may comprise a database. As used herein, the term "database" may refer to either a body of data, a relational database management system (RDBMS), or to both. As used herein, a database may comprise any collection of data including hierarchical databases, relational databases, flat file databases, object-relational databases, object-oriented databases, distributed databases, and any other structured collection of records or data that is stored in a computer system. Examples of RDBMS's include, but are not limited to including, ORACLE®, MYSQL, IBM® DB2, MICROSOFT® SQL SERVER, SYBASE®, and POSTGRESQL databases. However, any database may be used that enables the systems and methods described herein.

When field data 106 is not provided directly to the agricultural intelligence computer system via one or more agricultural machines or agricultural machine devices that interacts with the agricultural intelligence computer system, the user may be prompted via one or more user interfaces on the user device (served by the agricultural intelligence computer system) to input such information. In an example embodiment, the user may specify identification data by accessing a map on the user device (served by the agricultural intelligence computer system) and selecting specific CLUs that have been graphically shown on the map. In an alternative embodiment, the user 102 may specify identification data by accessing a map on the user device (served by the agricultural intelligence computer system 130) and drawing boundaries of the field over the map. Such CLU selection or map drawings represent geographic identifiers. In alternative embodiments, the user may specify identification data by accessing field identification data (provided as shape files or in a similar format) from the U.S. Department of Agriculture Farm Service Agency or other source via the user device and providing such field identification data to the agricultural intelligence computer system.

In an example embodiment, the agricultural intelligence computer system 130 is programmed to generate and cause displaying a graphical user interface comprising a data manager for data input. After one or more fields have been identified using the methods described above, the data manager may provide one or more graphical user interface widgets which when selected can identify changes to the field, soil, crops, tillage, or nutrient practices. The data manager may include a timeline view, a spreadsheet view, and/or one or more editable programs.

Figure 5:
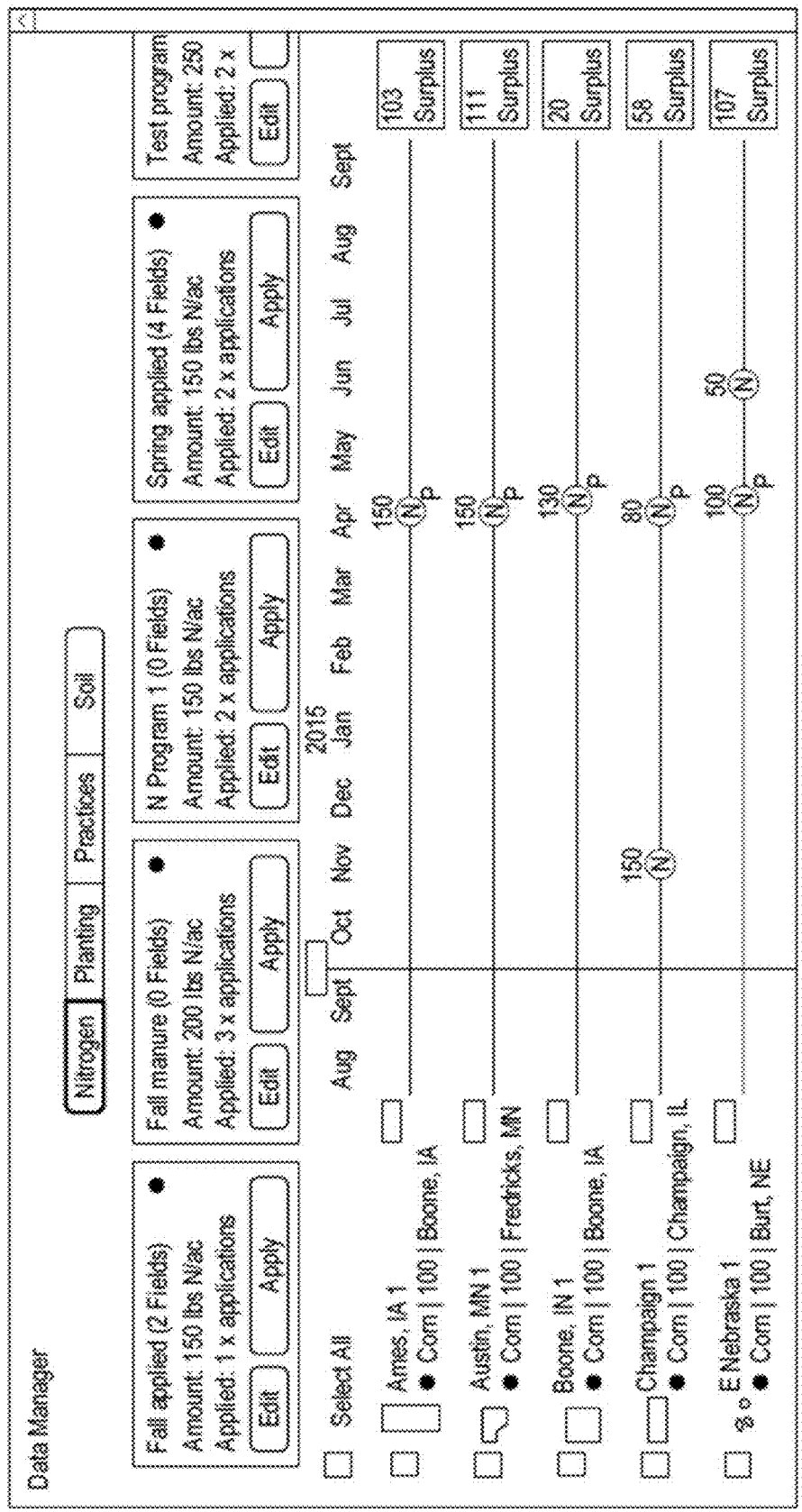
FIG. 5 depicts an example embodiment of a timeline view for data entry.

FIG. 5 depicts an example embodiment of a timeline view for data entry. Using the display depicted in FIG. 5, a user computer can input a selection of a particular field and a particular date for the addition of event. Events depicted at the top of the timeline may include Nitrogen, Planting, Practices, and Soil. To add a nitrogen application event, a user computer may provide input to select the nitrogen tab. The user computer may then select a location on the timeline for a particular field in order to indicate an application of nitrogen on the selected field. In response to receiving a selection of a location on the timeline for a particular field, the data manager may display a data entry overlay, allowing the user computer to input data pertaining to nitrogen applications, planting procedures, soil application, tillage procedures, irrigation practices, or other information relating to the particular field. For example, if a user computer selects a portion of the timeline and indicates an application of nitrogen, then the data entry overlay may include fields for inputting an amount of nitrogen applied, a date of application, a type of fertilizer used, and any other information related to the application of nitrogen.

In an embodiment, the data manager provides an interface for creating one or more programs. "Program," in this context, refers to a set of data pertaining to nitrogen applications, planting procedures, soil application, tillage procedures, irrigation practices, or other information that may be related to one or more fields, and that can be stored in digital data storage for reuse as a set to be used in other operations. After a program has been created, it may be conceptually applied to one or more fields and references to the program may be stored in digital storage in association with data identifying the fields. Thus, instead of manually entering identical data relating to the same nitrogen applications for multiple different fields, a user computer may create a program that indicates a particular application of nitrogen and then apply the program to multiple different fields. For example, in the timeline view of FIG. 5, the top two timelines have the "Spring applied" program selected, which includes an application of 150 lbs N/ac in early April. The data manager may provide an interface for editing a program. In an embodiment, when a particular program is edited, each field that has selected the particular program is edited. For example, in FIG. 5, if the "Spring applied" program is edited to reduce the application of nitrogen to 130 lbs. N/ac, the top two fields may be updated with a reduced application of nitrogen based on the edited program.

In an embodiment, in response to receiving edits to a field that has a program selected, the data manager removes the correspondence of the field to the selected program. For example, if a nitrogen application is added to the top field in FIG. 5, the interface may update to indicate that the "Spring applied" program is no longer being applied to the top field. While the nitrogen application in early April may remain, updates to the "Spring applied" program would not alter the April application of nitrogen.

Figure 6:
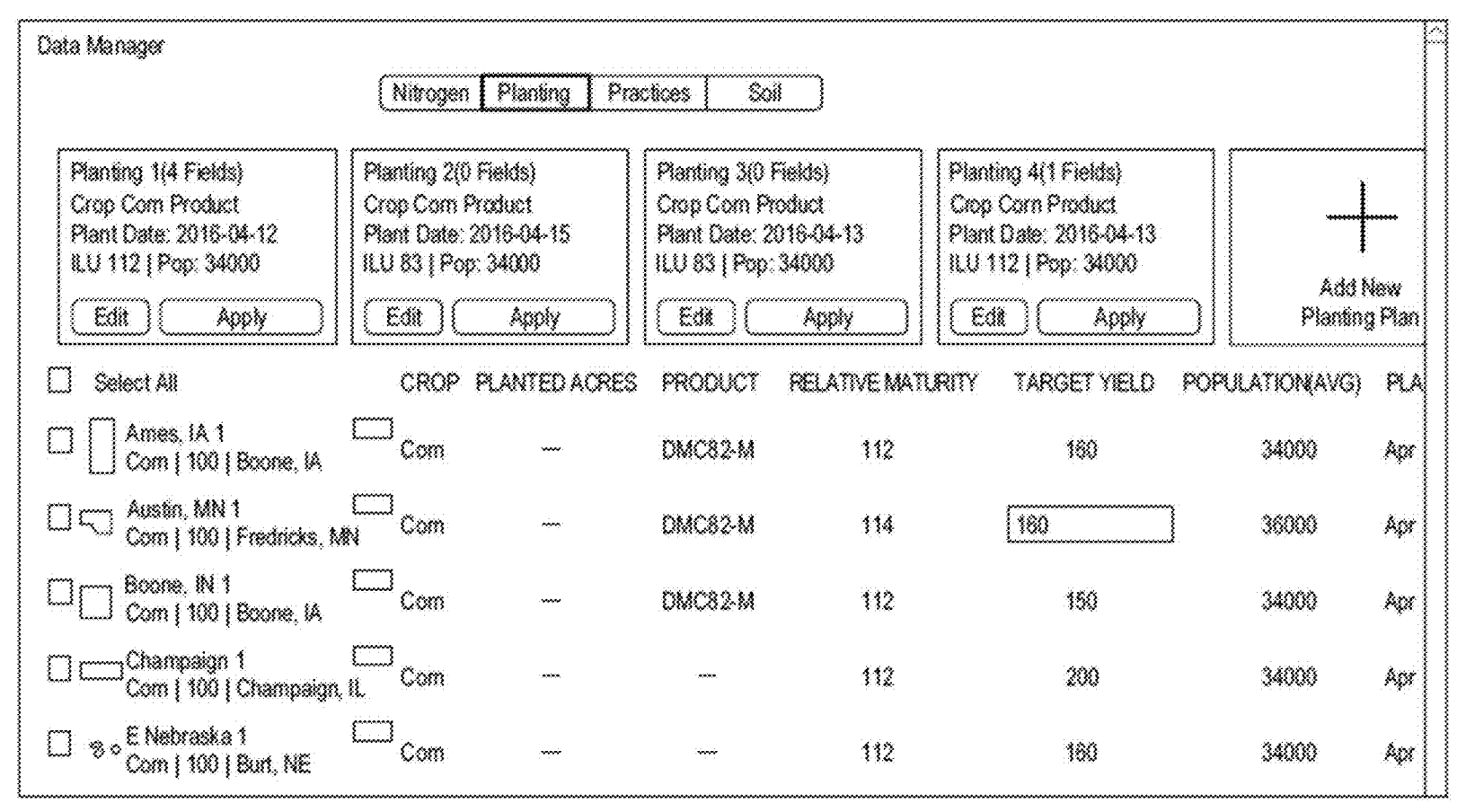

FIG. 6 depicts an example embodiment of a spreadsheet view for data entry. Using the display depicted in FIG. 6, a user can create and edit information for one or more fields. The data manager may include spreadsheets for inputting information with respect to Nitrogen, Planting, Practices, and Soil as depicted in FIG. 6. To edit a particular entry, a user computer may select the particular entry in the spreadsheet and update the values. For example, FIG. 6 depicts an in-progress update to a target yield value for the second field. Additionally, a user computer may select one or more fields in order to apply one or more programs. In response to receiving a selection of a program for a particular field, the data manager may automatically complete the entries for the particular field based on the selected program. As with the timeline view, the data manager may update the entries for each field associated with a particular program in response to receiving an update to the program. Additionally, the data manager may remove the correspondence of the selected program to the field in response to receiving an edit to one of the entries for the field.

In an embodiment, model and field data is stored in model and field data repository 160. Model data comprises data models created for one or more fields. For example, a crop model may include a digitally constructed model of the development of a crop on the one or more fields. "Model," in this context, refers to an electronic digitally stored set of executable instructions and data values, associated with one another, which are capable of receiving and responding to a programmatic or other digital call, invocation, or request for resolution based upon specified input values, to yield one or more stored or calculated output values that can serve as the basis of computer-implemented recommendations, output data displays, or machine control, among other things. Persons of skill in the field find it convenient to express models using mathematical equations, but that form of expression does not confine the models disclosed herein to abstract concepts; instead, each model herein has a practical application in a computer in the form of stored executable instructions and data that implement the model using the computer. The model may include a model of past events on the one or more fields, a model of the current status of the one or more fields, and/or a model of predicted events on the one or more fields. Model and field data may be stored in data structures in memory, rows in a database table, in flat files or spreadsheets, or other forms of stored digital data.

In some embodiments, agricultural intelligence computer system 130 is programmed with or comprises a soil analysis server ("server") 170. The server 170 is further configured to comprise a soil property concentration analysis component 172 and a client interface 174. Each of the soil property concentration analysis component 172 and the client interface 174 may be implemented as sequences of stored program instructions. In some embodiments, the soil property concentration analysis component 172 is programmed to receive input data from one or more sources and output current concentration levels of a target analyte in the soil or recommendations for adjusting the current concentration levels. Input data to the soil property concentration analysis component 172 can include data generated by an in-ground sensor system with modular sensors, processors, and wireless communications components for monitoring properties of field soils introduced above and to be further discussed in in FIG. 8, which can comprise one or more of the agricultural apparatus 111, the application controller 114, and the remote sensor 112. An example of such data would be current nitrate concentration levels in certain soil samples. Additional input data can include data received from user computers, such as the field manager computing device 104 or the cab computer 115, or from the data server computer 108, or other data that have been stored in the model data field data repository 160, such as expected crop yield levels, soil nutrient loss history, historical weather reports or weather forecasts, or records of applying other types of soil nutrients. Output data from the soil property concentration analysis component 172 can include when and how to adjust concentration levels of certain soil nutrients or other elements as well as where such adjustment should be applied. Such data can be communicated to the user computers or other remote computers.

In some embodiments, the client interface 174 is configured to manage communication with the in-ground sensor system or a user computer over a communication network, through the communication layer 132. The communication can include receiving instructions to start real-time field measurements and desired soil condition or production level from a user computer, sending instructions to the mobile soil analysis system for performing real-time measurements of soil element concentration levels, receiving the soil measurements from the mobile soil analysis system, and sending results of analyzing the soil measurements with respect to the desired soil condition or production level to the user computer.

Each component of the server 170 comprises a set of one or more pages of main memory, such as RAM, in the agricultural intelligence computer system 130 into which executable instructions have been loaded and which when executed cause the agricultural intelligence computing system to perform the functions or operations that are described herein with reference to those modules. For example, the soil element concentration analysis component 172 may comprise a set of pages in RAM that contain instructions which when executed cause performing soil element concentration analysis described herein. The instructions may be in machine executable code in the instruction set of a CPU and may have been compiled based upon source code written in JAVA, C, C++, OBJECTIVE-C, or any other human-readable programming language or environment, alone or in combination with scripts in JAVASCRIPT, other scripting languages and other programming source text. The term "pages" is intended to refer broadly to any region within main memory and the specific terminology used in a system may vary depending on the memory architecture or processor architecture. In another embodiment, each of the components in the server 170 also may represent one or more files or projects of source code that are digitally stored in a mass storage device such as non-volatile RAM or disk storage, in the agricultural intelligence computer system 130 or a separate repository system, which when compiled or interpreted cause generating executable instructions which when executed cause the agricultural intelligence computing system to perform the functions or operations that are described herein with reference to those modules. In other words, the drawing figure may represent the manner in which programmers or software developers organize and arrange source code for later compilation into an executable, or interpretation into bytecode or the equivalent, for execution by the agricultural intelligence computer system 130.

Figure 4:
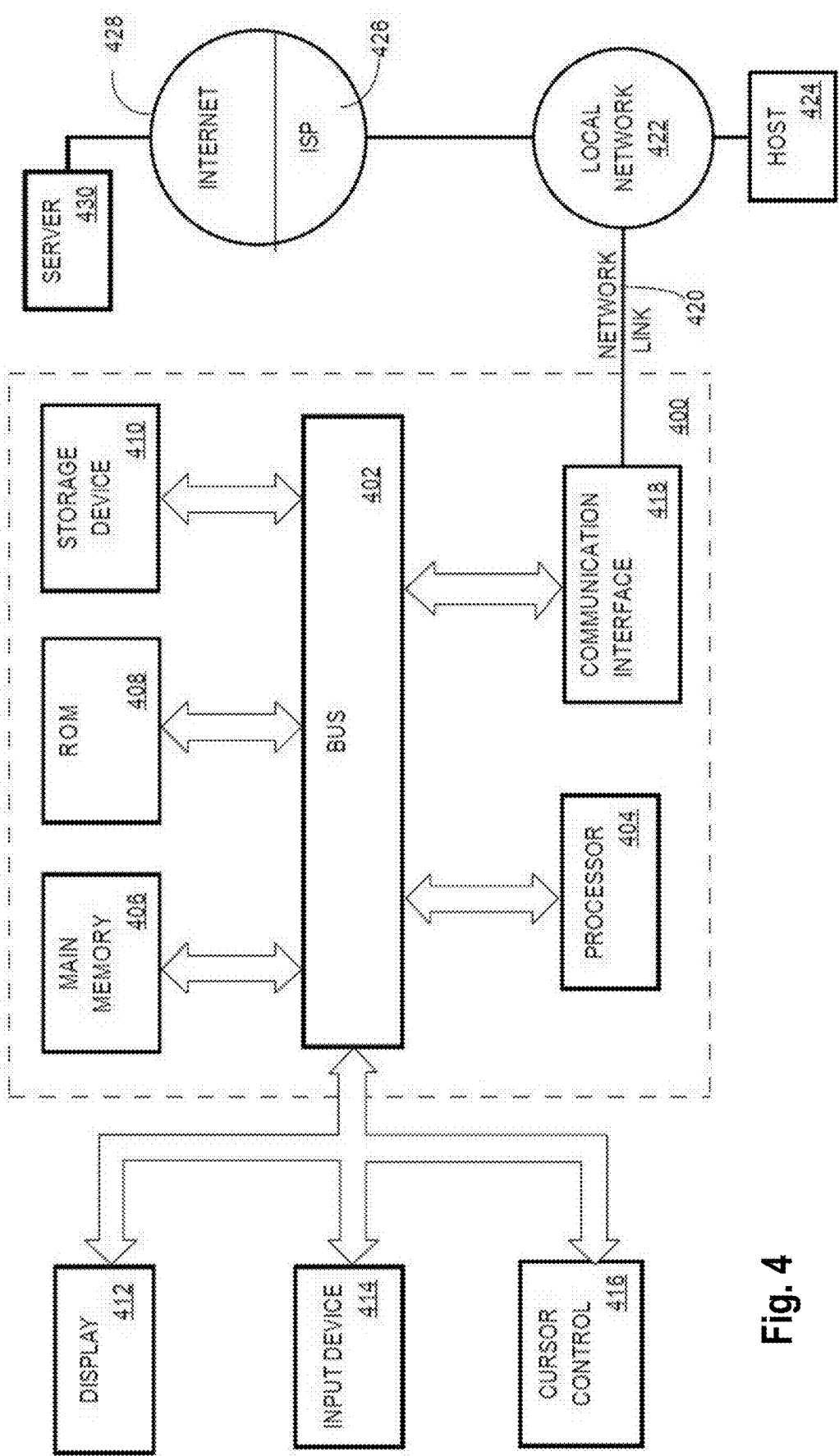
FIG. 4 is a block diagram that illustrates a computer system upon which an embodiment of the invention may be implemented.

Hardware/virtualization layer 150 comprises one or more central processing units (CPUs), memory controllers, and other devices, components, or elements of a computer system such as volatile or non-volatile memory, non-volatile storage such as disk, and I/O devices or interfaces as illustrated and described, for example, in connection with FIG. 4. The layer 150 also may comprise programmed instructions that are configured to support virtualization, containerization, or other technologies.

For purposes of illustrating a clear example, FIG. 1 shows a limited number of instances of certain functional elements. However, in other embodiments, there may be any number of such elements. For example, embodiments may use thousands or millions of different mobile computing devices 104 associated with different users. Further, the system 130 and/or external data server computer 108 may be implemented using two or more processors, cores, clusters, or instances of physical machines or virtual machines, configured in a discrete location or co-located with other elements in a datacenter, shared computing facility or cloud computing facility.

2.2. Application Program Overview

In an embodiment, the implementation of the functions described herein using one or more computer programs or other software elements that are loaded into and executed using one or more general-purpose computers will cause the general-purpose computers to be configured as a particular machine or as a computer that is specially adapted to perform the functions described herein. Further, each of the flow diagrams that are described further herein may serve, alone or in combination with the descriptions of processes and functions in prose herein, as algorithms, plans or directions that may be used to program a computer or logic to implement the functions that are described. In other words, all the prose text herein, and all the drawing figures, together are intended to provide disclosure of algorithms, plans or directions that are sufficient to permit a skilled person to program a computer to perform the functions that are described herein, in combination with the skill and knowledge of such a person given the level of skill that is appropriate for inventions and disclosures of this type.

In an embodiment, user 102 interacts with agricultural intelligence computer system 130 using field manager computing device 104 configured with an operating system and one or more application programs or apps; the field manager computing device 104 also may interoperate with the agricultural intelligence computer system independently and automatically under program control or logical control and direct user interaction is not always required. Field manager computing device 104 broadly represents one or more smartphones, PDA, tablet computing device, laptop computer, desktop computer, workstation, or any other computing device capable of transmitting and receiving information and performing the functions described herein. Field manager computing device 104 may communicate via a network using a mobile application stored on field manager computing device 104, and in some embodiments, the device may be coupled using a cable 113 or connector to the sensor 112 and/or controller 114. A particular user 102 may own, operate or possess and use, in connection with system 130, more than one field manager computing device 104 at a time.

The mobile application may provide client-side functionality, via the network to one or more mobile computing devices. In an example embodiment, field manager computing device 104 may access the mobile application via a web browser or a local client application or app. Field manager computing device 104 may transmit data to, and receive data from, one or more front-end servers, using web-based protocols or formats such as HTTP, XML, and/or JSON, or app-specific protocols. In an example embodiment, the data may take the form of requests and user information input, such as field data, into the mobile computing device. In some embodiments, the mobile application interacts with location tracking hardware and software on field manager computing device 104 which determines the location of field manager computing device 104 using standard tracking techniques such as multilateration of radio signals, the global positioning system (GPS), Wi-Fi positioning systems, or other methods of mobile positioning. In some cases, location data or other data associated with the device 104, user 102, and/or user account(s) may be obtained by queries to an operating system of the device or by requesting an app on the device to obtain data from the operating system.

In an embodiment, field manager computing device 104 sends field data 106 to agricultural intelligence computer system 130 comprising or including, but not limited to, data values representing one or more of: a geographical location of the one or more fields, tillage information for the one or more fields, crops planted in the one or more fields, and soil data extracted from the one or more fields. Field manager computing device 104 may send field data 106 in response to user input from user 102 specifying the data values for the one or more fields. Additionally, field manager computing device 104 may automatically send field data 106 when one or more of the data values becomes available to field manager computing device 104. For example, field manager computing device 104 may be communicatively coupled to remote sensor 112 and/or application controller 114 which include an irrigation sensor and/or irrigation controller. In response to receiving data indicating that application controller 114 released water onto the one or more fields, field manager computing device 104 may send field data 106 to agricultural intelligence computer system 130 indicating that water was released on the one or more fields. Field data 106 identified in this disclosure may be input and communicated using electronic digital data that is communicated between computing devices using parameterized URLs over HTTP, or another suitable communication or messaging protocol.

A commercial example of the mobile application is CLIMATE FIELDVIEW, commercially available from The Climate Corporation, San Francisco, California. The CLIMATE FIELDVIEW application, or other applications, may be modified, extended, or adapted to include features, functions, and programming that have not been disclosed earlier than the filing date of this disclosure. In one embodiment, the mobile application comprises an integrated software platform that allows a grower to make fact-based decisions for their operation because it combines historical data about the grower's fields with any other data that the grower wishes to compare. The combinations and comparisons may be performed in real time and are based upon scientific models that provide potential scenarios to permit the grower to make better, more informed decisions.

FIG. 2 illustrates two views of an example logical organization of sets of instructions in main memory when an example mobile application is loaded for execution. In FIG. 2, each named element represents a region of one or more pages of RAM or other main memory, or one or more blocks of disk storage or other non-volatile storage, and the programmed instructions within those regions. In one embodiment, in view (a), a mobile computer application 200 comprises account-fields-data ingestion-sharing instructions 202, overview and alert instructions 204, digital map book instructions 206, seeds and planting instructions 208, nitrogen instructions 210, weather instructions 212, field health instructions 214, and performance instructions 216.

In one embodiment, a mobile computer application 200 comprises account, fields, data ingestion, sharing instructions 202 which are programmed to receive, translate, and ingest field data from third party systems via manual upload or APIs. Data types may include field boundaries, yield maps, as-planted maps, soil test results, as-applied maps, and/or management zones, among others. Data formats may include shapefiles, native data formats of third parties, and/or farm management information system (FMIS) exports, among others. Receiving data may occur via manual upload, email with attachment, external APIs that push data to the mobile application, or instructions that call APIs of external systems to pull data into the mobile application. In one embodiment, mobile computer application 200 comprises a data inbox. In response to receiving a selection of the data inbox, the mobile computer application 200 may display a graphical user interface for manually uploading data files and importing uploaded files to a data manager.

In one embodiment, digital map book instructions 206 comprise field map data layers stored in device memory and are programmed with data visualization tools and geospatial field notes. This provides growers with convenient information close at hand for reference, logging and visual insights into field performance. In one embodiment, overview and alert instructions 204 are programmed to provide an operation-wide view of what is important to the grower, and timely recommendations to take action or focus on particular issues. This permits the grower to focus time on what needs attention, to save time and preserve yield throughout the season. In one embodiment, seeds and planting instructions 208 are programmed to provide tools for seed selection, hybrid placement, and script creation, including variable rate (VR) script creation, based upon scientific models and empirical data. This enables growers to maximize yield or return on investment through optimized seed purchase, placement and population.

In one embodiment, script generation instructions 205 are programmed to provide an interface for generating scripts, including variable rate (VR) fertility scripts. The interface enables growers to create scripts for field implements, such as nutrient applications, planting, and irrigation. For example, a planting script interface may comprise tools for identifying a type of seed for planting. Upon receiving a selection of the seed type, mobile computer application 200 may display one or more fields broken into management zones, such as the field map data layers created as part of digital map book instructions 206. In one embodiment, the management zones comprise soil zones along with a panel identifying each soil zone and a soil name, texture, drainage for each zone, or other field data. Mobile computer application 200 may also display tools for editing or creating such, such as graphical tools for drawing management zones, such as soil zones, over a map of one or more fields. Planting procedures may be applied to all management zones or different planting procedures may be applied to different subsets of management zones. When a script is created, mobile computer application 200 may make the script available for download in a format readable by an application controller, such as an archived or compressed format. Additionally, and/or alternatively, a script may be sent directly to cab computer 115 from mobile computer application 200 and/or uploaded to one or more data servers and stored for further use.

In one embodiment, nitrogen instructions 210 are programmed to provide tools to inform nitrogen decisions by visualizing the availability of nitrogen to crops. This enables growers to maximize yield or return on investment through optimized nitrogen application during the season. Example programmed functions include displaying images such as SSURGO images to enable drawing of fertilizer application zones and/or images generated from subfield soil data, such as data obtained from sensors, at a high spatial resolution (as fine as millimeters or smaller depending on sensor proximity and resolution); upload of existing grower-defined zones; providing a graph of plant nutrient availability and/or a map to enable tuning application(s) of nitrogen across multiple zones; output of scripts to drive machinery; tools for mass data entry and adjustment; and/or maps for data visualization, among others. "Mass data entry," in this context, may mean entering data once and then applying the same data to multiple fields and/or zones that have been defined in the system; example data may include nitrogen application data that is the same for many fields and/or zones of the same grower, but such mass data entry applies to the entry of any type of field data into the mobile computer application 200. For example, nitrogen instructions 210 may be programmed to accept definitions of nitrogen application and practices programs and to accept user input specifying to apply those programs across multiple fields. "Nitrogen application programs," in this context, refers to stored, named sets of data that associates: a name, color code or other identifier, one or more dates of application, types of material or product for each of the dates and amounts, method of application or incorporation such as injected or broadcast, and/or amounts or rates of application for each of the dates, crop or hybrid that is the subject of the application, among others. "Nitrogen practices programs," in this context, refer to stored, named sets of data that associates: a practices name; a previous crop; a tillage system; a date of primarily tillage; one or more previous tillage systems that were used; one or more indicators of application type, such as manure, that were used. Nitrogen instructions 210 also may be programmed to generate and cause displaying a nitrogen graph, which indicates projections of plant use of the specified nitrogen and whether a surplus or shortfall is predicted; in some embodiments, different color indicators may signal a magnitude of surplus or magnitude of shortfall. In one embodiment, a nitrogen graph comprises a graphical display in a computer display device comprising a plurality of rows, each row associated with and identifying a field; data specifying what crop is planted in the field, the field size, the field location, and a graphic representation of the field perimeter; in each row, a timeline by month with graphic indicators specifying each nitrogen application and amount at points correlated to month names; and numeric and/or colored indicators of surplus or shortfall, in which color indicates magnitude.

In one embodiment, the nitrogen graph may include one or more user input features, such as dials or slider bars, to dynamically change the nitrogen planting and practices programs so that a user may optimize his nitrogen graph. The user may then use his optimized nitrogen graph and the related nitrogen planting and practices programs to implement one or more scripts, including variable rate (VR) fertility scripts. Nitrogen instructions 210 also may be programmed to generate and cause displaying a nitrogen map, which indicates projections of plant use of the specified nitrogen and whether a surplus or shortfall is predicted; in some embodiments, different color indicators may signal a magnitude of surplus or magnitude of shortfall. The nitrogen map may display projections of plant use of the specified nitrogen and whether a surplus or shortfall is predicted for different times in the past and the future (such as daily, weekly, monthly or yearly) using numeric and/or colored indicators of surplus or shortfall, in which color indicates magnitude. In one embodiment, the nitrogen map may include one or more user input features, such as dials or slider bars, to dynamically change the nitrogen planting and practices programs so that a user may optimize his nitrogen map, such as to obtain a preferred amount of surplus to shortfall. The user may then use his optimized nitrogen map and the related nitrogen planting and practices programs to implement one or more scripts, including variable rate (VR) fertility scripts. In other embodiments, similar instructions to the nitrogen instructions 210 could be used for application of other nutrients (such as phosphorus and potassium), application of pesticide, and irrigation programs.

In one embodiment, weather instructions 212 are programmed to provide field-specific recent weather data and forecasted weather information. This enables growers to save time and have an efficient integrated display with respect to daily operational decisions.

In one embodiment, field health instructions 214 are programmed to provide timely remote sensing images highlighting in-season crop variation and potential concerns. Example programmed functions include cloud checking, to identify possible clouds or cloud shadows; determining nitrogen indices based on field images; graphical visualization of scouting layers, including, for example, those related to field health, and viewing and/or sharing of scouting notes; and/or downloading satellite images from multiple sources and prioritizing the images for the grower, among others.

In one embodiment, performance instructions 216 are programmed to provide reports, analysis, and insight tools using on-farm data for evaluation, insights and decisions. This enables the grower to seek improved outcomes for the next year through fact-based conclusions about why return on investment was at prior levels, and insight into yield-limiting factors. The performance instructions 216 may be programmed to communicate via the network(s) 109 to back-end analytics programs executed at agricultural intelligence computer system 130 and/or external data server computer 108 and configured to analyze metrics such as yield, yield differential, hybrid, population, SSURGO zone, soil test properties, or elevation, among others. Programmed reports and analysis may include yield variability analysis, treatment effect estimation, benchmarking of yield and other metrics against other growers based on anonymized data collected from many growers, or data for seeds and planting, among others.

Applications having instructions configured in this way may be implemented for different computing device platforms while retaining the same general user interface appearance. For example, the mobile application may be programmed for execution on tablets, smartphones, or server computers that are accessed using browsers at client computers. Further, the mobile application as configured for tablet computers or smartphones may provide a full app experience or a cab app experience that is suitable for the display and processing capabilities of cab computer 115. For example, referring now to view (b) of FIG. 2, in one embodiment a cab computer application 220 may comprise maps-cab instructions 222, remote view instructions 224, data collect and transfer instructions 226, machine alerts instructions 228, script transfer instructions 230, and scouting-cab instructions 232. The code base for the instructions of view (b) may be the same as for view (a) and executables implementing the code may be programmed to detect the type of platform on which they are executing and to expose, through a graphical user interface, only those functions that are appropriate to a cab platform or full platform. This approach enables the system to recognize the distinctly different user experience that is appropriate for an in-cab environment and the different technology environment of the cab. The maps-cab instructions 222 may be programmed to provide map views of fields, farms or regions that are useful in directing machine operation. The remote view instructions 224 may be programmed to turn on, manage, and provide views of machine activity in real-time or near real-time to other computing devices connected to the system 130 via wireless networks, wired connectors or adapters, and the like. The data collect and transfer instructions 226 may be programmed to turn on, manage, and provide transfer of data collected at sensors and controllers to the system 130 via wireless networks, wired connectors or adapters, and the like. The machine alerts instructions 228 may be programmed to detect issues with operations of the machine or tools that are associated with the cab and generate operator alerts. The script transfer instructions 230 may be configured to transfer in scripts of instructions that are configured to direct machine operations or the collection of data. The scouting-cab instructions 232 may be programmed to display location-based alerts and information received from the system 130 based on the location of the field manager computing device 104, agricultural apparatus 111, or sensors 112 in the field and ingest, manage, and provide transfer of location-based scouting observations to the system 130 based on the location of the agricultural apparatus 111 or sensors 112 in the field.

2.3. Data Ingest to the Computer System

In an embodiment, external data server computer 108 stores external data 110, including soil data representing soil composition for the one or more fields and weather data representing temperature and precipitation on the one or more fields. The weather data may include past and present weather data as well as forecasts for future weather data. In an embodiment, external data server computer 108 comprises a plurality of servers hosted by different entities. For example, a first server may contain soil composition data while a second server may include weather data. Additionally, soil composition data may be stored in multiple servers. For example, one server may store data representing percentage of sand, silt, and clay in the soil while a second server may store data representing percentage of organic matter (OM) in the soil.

In an embodiment, remote sensor 112 comprises one or more sensors that are programmed or configured to produce one or more observations. Remote sensor 112 may be aerial sensors, such as satellites, vehicle sensors, planting equipment sensors, tillage sensors, fertilizer or insecticide application sensors, harvester sensors, and any other implement capable of receiving data from the one or more fields. In an embodiment, application controller 114 is programmed or configured to receive instructions from agricultural intelligence computer system 130. Application controller 114 may also be programmed or configured to control an operating parameter of an agricultural vehicle or implement. For example, an application controller may be programmed or configured to control an operating parameter of a vehicle, such as a tractor, planting equipment, tillage equipment, fertilizer or insecticide equipment, harvester equipment, or other farm implements such as a water valve. Other embodiments may use any combination of sensors and controllers, of which the following are merely selected examples.

The system 130 may obtain or ingest data under user 102 control, on a mass basis from a large number of growers who have contributed data to a shared database system. This form of obtaining data may be termed "manual data ingest" as one or more user-controlled computer operations are requested or triggered to obtain data for use by the system 130. As an example, the CLIMATE FIELDVIEW application, commercially available from The Climate Corporation, San Francisco, California, may be operated to export data to system 130 for storing in the repository 160.

For example, seed monitor systems can both control planter apparatus components and obtain planting data, including signals from seed sensors via a signal harness that comprises a CAN backbone and point-to-point connections for registration and/or diagnostics. Seed monitor systems can be programmed or configured to display seed spacing, population and other information to the user via the cab computer 115 or other devices within the system 130. Examples are disclosed in U.S. Pat. No. 8,738,243 and US Pat. Pub. 20150094916, and the present disclosure assumes knowledge of those other patent disclosures.

Likewise, yield monitor systems may contain yield sensors for harvester apparatus that send yield measurement data to the cab computer 115 or other devices within the system 130. Yield monitor systems may utilize one or more remote sensors 112 to obtain grain moisture measurements in a combine or other harvester and transmit these measurements to the user via the cab computer 115 or other devices within the system 130.

In an embodiment, examples of sensors 112 that may be used with any moving vehicle or apparatus of the type described elsewhere herein include kinematic sensors and position sensors. Kinematic sensors may comprise any of speed sensors such as radar or wheel speed sensors, accelerometers, or gyros. Position sensors may comprise GPS receivers or transceivers, or Wi-Fi-based position or mapping apps that are programmed to determine location based upon nearby Wi-Fi hotspots, among others.

In an embodiment, examples of sensors 112 that may be used with tractors or other moving vehicles include engine speed sensors, fuel consumption sensors, area counters or distance counters that interact with GPS or radar signals, PTO (power take-off) speed sensors, tractor hydraulics sensors configured to detect hydraulics parameters such as pressure or flow, and/or and hydraulic pump speed, wheel speed sensors or wheel slippage sensors. In an embodiment, examples of controllers 114 that may be used with tractors include hydraulic directional controllers, pressure controllers, and/or flow controllers; hydraulic pump speed controllers; speed controllers or governors; hitch position controllers; or wheel position controllers provide automatic steering.

In an embodiment, examples of sensors 112 that may be used with seed planting equipment such as planters, drills, or air seeders include seed sensors, which may be optical, electromagnetic, or impact sensors; downforce sensors such as load pins, load cells, pressure sensors; soil property sensors such as reflectivity sensors, moisture sensors, electrical conductivity sensors, optical residue sensors, or temperature sensors; component operating criteria sensors such as planting depth sensors, downforce cylinder pressure sensors, seed disc speed sensors, seed drive motor encoders, seed conveyor system speed sensors, or vacuum level sensors; or pesticide application sensors such as optical or other electromagnetic sensors, or impact sensors. In an embodiment, examples of controllers 114 that may be used with such seed planting equipment include: toolbar fold controllers, such as controllers for valves associated with hydraulic cylinders; downforce controllers, such as controllers for valves associated with pneumatic cylinders, airbags, or hydraulic cylinders, and programmed for applying downforce to individual row units or an entire planter frame; planting depth controllers, such as linear actuators; metering controllers, such as electric seed meter drive motors, hydraulic seed meter drive motors, or swath control clutches; hybrid selection controllers, such as seed meter drive motors, or other actuators programmed for selectively allowing or preventing seed or an air-seed mixture from delivering seed to or from seed meters or central bulk hoppers; metering controllers, such as electric seed meter drive motors, or hydraulic seed meter drive motors; seed conveyor system controllers, such as controllers for a belt seed delivery conveyor motor; marker controllers, such as a controller for a pneumatic or hydraulic actuator; or pesticide application rate controllers, such as metering drive controllers, orifice size or position controllers.

In an embodiment, examples of sensors 112 that may be used with tillage equipment include position sensors for tools such as shanks or discs; tool position sensors for such tools that are configured to detect depth, gang angle, or lateral spacing; downforce sensors; or draft force sensors. In an embodiment, examples of controllers 114 that may be used with tillage equipment include downforce controllers or tool position controllers, such as controllers configured to control tool depth, gang angle, or lateral spacing.

In an embodiment, examples of sensors 112 that may be used in relation to apparatus for applying fertilizer, insecticide, fungicide and the like, such as on-planter starter fertilizer systems, subsoil fertilizer applicators, or fertilizer sprayers, include: fluid system criteria sensors, such as flow sensors or pressure sensors; sensors indicating which spray head valves or fluid line valves are open; sensors associated with tanks, such as fill level sensors; sectional or system-wide supply line sensors, or row-specific supply line sensors; or kinematic sensors such as accelerometers disposed on sprayer booms. In an embodiment, examples of controllers 114 that may be used with such apparatus include pump speed controllers; valve controllers that are programmed to control pressure, flow, direction, PWM and the like; or position actuators, such as for boom height, subsoiler depth, or boom position.

In an embodiment, examples of sensors 112 that may be used with harvesters include yield monitors, such as impact plate strain gauges or position sensors, capacitive flow sensors, load sensors, weight sensors, or torque sensors associated with elevators or augers, or optical or other electromagnetic grain height sensors; grain moisture sensors, such as capacitive sensors; grain loss sensors, including impact, optical, or capacitive sensors; header operating criteria sensors such as header height, header type, deck plate gap, feeder speed, and reel speed sensors; separator operating criteria sensors, such as concave clearance, rotor speed, shoe clearance, or chaffer clearance sensors; auger sensors for position, operation, or speed; or engine speed sensors. In an embodiment, examples of controllers 114 that may be used with harvesters include header operating criteria controllers for elements such as header height, header type, deck plate gap, feeder speed, or reel speed; separator operating criteria controllers for features such as concave clearance, rotor speed, shoe clearance, or chaffer clearance; or controllers for auger position, operation, or speed.

In an embodiment, examples of sensors 112 that may be used with grain carts include weight sensors, or sensors for auger position, operation, or speed. In an embodiment, examples of controllers 114 that may be used with grain carts include controllers for auger position, operation, or speed.

In an embodiment, examples of sensors 112 and controllers 114 may be installed in unmanned aerial vehicle (UAV) apparatus or "drones." Such sensors may include cameras with detectors effective for any range of the electromagnetic spectrum including visible light, infrared, ultraviolet, near-infrared (NIR), and the like; accelerometers; altimeters; temperature sensors; humidity sensors; pitot tube sensors or other airspeed or wind velocity sensors; battery life sensors; or radar emitters and reflected radar energy detection apparatus; other electromagnetic radiation emitters and reflected electromagnetic radiation detection apparatus. Such controllers may include guidance or motor control apparatus, control surface controllers, camera controllers, or controllers programmed to turn on, operate, obtain data from, manage and configure any of the foregoing sensors. Examples are disclosed in U.S. patent application Ser. No. 14/831,165 and the present disclosure assumes knowledge of that other patent disclosure.

In an embodiment, sensors 112 and controllers 114 may be affixed to soil sampling and measurement apparatus that is configured or programmed to sample soil and perform soil chemistry tests, soil moisture tests, and other tests pertaining to soil. For example, the apparatus disclosed in U.S. Pat. Nos. 8,767,194 and 8,712,148 may be used, and the present disclosure assumes knowledge of those patent disclosures.

In an embodiment, sensors 112 and controllers 114 may comprise weather devices for monitoring weather conditions of fields. For example, the apparatus disclosed in U.S. Provisional Application No. 62/154,207, filed on Apr. 29, 2015, U.S. Provisional Application No. 62/175,160, filed on Jun. 12, 2015, U.S. Provisional Application No. 62/198,060, filed on Jul. 28, 2015, and U.S. Provisional Application No. 62/220,852, filed on Sep. 18, 2015, may be used, and the present disclosure assumes knowledge of those patent disclosures.

2.4. Process Overview-Agronomic Model Training

In an embodiment, the agricultural intelligence computer system 130 is programmed or configured to create an agronomic model. In this context, an agronomic model is a data structure in memory of the agricultural intelligence computer system 130 that comprises field data 106, such as identification data and harvest data for one or more fields. The agronomic model may also comprise calculated agronomic properties which describe either conditions which may affect the growth of one or more crops on a field, or properties of the one or more crops, or both. Additionally, an agronomic model may comprise recommendations based on agronomic factors such as crop recommendations, irrigation recommendations, planting recommendations, fertilizer recommendations, fungicide recommendations, pesticide recommendations, harvesting recommendations and other crop management recommendations. The agronomic factors may also be used to estimate one or more crop related results, such as agronomic yield. The agronomic yield of a crop is an estimate of quantity of the crop that is produced, or in some examples the revenue or profit obtained from the produced crop.

In an embodiment, the agricultural intelligence computer system 130 may use a preconfigured agronomic model to calculate agronomic properties related to currently received location and crop information for one or more fields. The preconfigured agronomic model is based upon previously processed field data, including but not limited to, identification data, harvest data, fertilizer data, and weather data.

The preconfigured agronomic model may have been cross validated to ensure accuracy of the model. Cross validation may include comparison to ground truthing that compares predicted results with actual results on a field, such as a comparison of precipitation estimate with a rain gauge or sensor providing weather data at the same or nearby location or an estimate of nitrogen content with a soil sample measurement.

Figure 3:
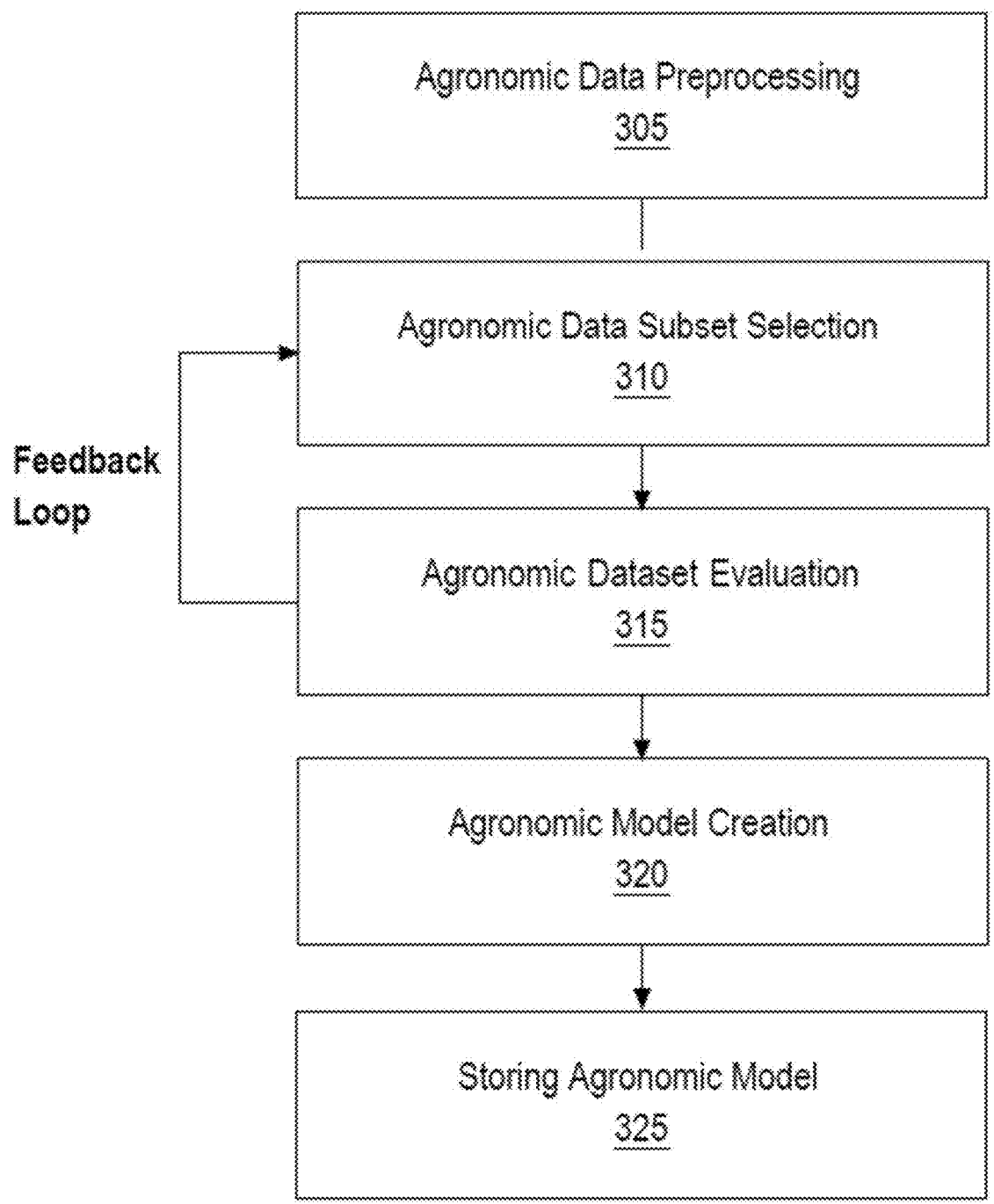
FIG. 3 depicts a programmed process by which the agricultural intelligence computer system generates one or more preconfigured agronomic models using agronomic data provided by one or more data sources.

FIG. 3 illustrates a programmed process by which the agricultural intelligence computer system generates one or more preconfigured agronomic models using field data provided by one or more data sources. FIG. 3 may serve as an algorithm or instructions for programming the functional elements of the agricultural intelligence computer system 130 to perform the operations that are now described.

At block 305, the agricultural intelligence computer system 130 is configured or programmed to implement agronomic data preprocessing of field data received from one or more data sources. The field data received from one or more data sources may be preprocessed for the purpose of removing noise, distorting effects, and confounding factors within the agronomic data including measured outliers that could adversely affect received field data values. Embodiments of agronomic data preprocessing may include, but are not limited to, removing data values commonly associated with outlier data values, specific measured data points that are known to unnecessarily skew other data values, data smoothing, aggregation, or sampling techniques used to remove or reduce additive or multiplicative effects from noise, and other filtering or data derivation techniques used to provide clear distinctions between positive and negative data inputs.

At block 310, the agricultural intelligence computer system 130 is configured or programmed to perform data subset selection using the preprocessed field data in order to identify datasets useful for initial agronomic model generation. The agricultural intelligence computer system 130 may implement data subset selection techniques including, but not limited to, a genetic algorithm method, an all subset models method, a sequential search method, a stepwise regression method, a particle swarm optimization method, and an ant colony optimization method. For example, a genetic algorithm selection technique uses an adaptive heuristic search algorithm, based on evolutionary principles of natural selection and genetics, to determine and evaluate datasets within the preprocessed agronomic data.

At block 315, the agricultural intelligence computer system 130 is configured or programmed to implement field dataset evaluation. In an embodiment, a specific field dataset is evaluated by creating an agronomic model and using specific quality thresholds for the created agronomic model. Agronomic models may be compared and/or validated using one or more comparison techniques, such as, but not limited to, root mean square error with leave-one-out cross validation (RMSECV), mean absolute error, and mean percentage error. For example, RMSECV can cross validate agronomic models by comparing predicted agronomic property values created by the agronomic model against historical agronomic property values collected and analyzed. In an embodiment, the agronomic dataset evaluation logic is used as a feedback loop where agronomic datasets that do not meet configured quality thresholds are used during future data subset selection steps (block 310).

At block 320, the agricultural intelligence computer system 130 is configured or programmed to implement agronomic model creation based upon the cross validated agronomic datasets. In an embodiment, agronomic model creation may implement multivariate regression techniques to create preconfigured agronomic data models.

At block 325, the agricultural intelligence computer system 130 is configured or programmed to store the preconfigured agronomic data models for future field data evaluation.

2.5. Implementation Example—Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

For example, FIG. 4 is a block diagram that illustrates a computer system 400 upon which an embodiment of the invention may be implemented. Computer system 400 includes a bus 402 or other communication mechanism for communicating information, and a hardware processor 404 coupled with bus 402 for processing information. Hardware processor 404 may be, for example, a general-purpose microprocessor.

Computer system 400 also includes a main memory 406, such as a random-access memory (RAM) or other dynamic storage device, coupled to bus 402 for storing information and instructions to be executed by processor 404. Main memory 406 also may be used for storing temporary variables or other intermediate information during execution of instructions to be executed by processor 404. Such instructions, when stored in non-transitory storage media accessible to processor 404, render computer system 400 into a special-purpose machine that is customized to perform the operations specified in the instructions.

Computer system 400 further includes a read only memory (ROM) 408 or other static storage device coupled to bus 402 for storing static information and instructions for processor 404. A storage device 410, such as a magnetic disk, optical disk, or solid-state drive is provided and coupled to bus 402 for storing information and instructions.

Computer system 400 may be coupled via bus 402 to a display 412, such as a cathode ray tube (CRT), for displaying information to a computer user. An input device 414, including alphanumeric and other keys, is coupled to bus 402 for communicating information and command selections to processor 404. Another type of user input device is cursor control 416, such as a mouse, a trackball, or cursor direction keys for communicating direction information and command selections to processor 404 and for controlling cursor movement on display 412. This input device typically has two degrees of freedom in two axes, a first axis (e.g., x) and a second axis (e.g., y), that allows the device to specify positions in a plane.

Computer system 400 may implement the techniques described herein using customized hard-wired logic, one or more ASICs or FPGAs, firmware and/or program logic which in combination with the computer system causes or programs computer system 400 to be a special-purpose machine. According to one embodiment, the techniques herein are performed by computer system 400 in response to processor 404 executing one or more sequences of one or more instructions contained in main memory 406. Such instructions may be read into main memory 406 from another storage medium, such as storage device 410. Execution of the sequences of instructions contained in main memory 406 causes processor 404 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage device 410. Volatile media includes dynamic memory, such as main memory 406. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 402. Transmission media can also take the form of acoustic or light waves, such as those generated during radio-wave and infrared data communications.

Various forms of media may be involved in carrying one or more sequences of one or more instructions to processor 404 for execution. For example, the instructions may initially be carried on a magnetic disk or solid-state drive of a remote computer. The remote computer can load the instructions into its dynamic memory and send the instructions over a telephone line using a modem. A modem local to computer system 400 can receive the data on the telephone line and use an infrared transmitter to convert the data to an infrared signal. An infrared detector can receive the data carried in the infrared signal and appropriate circuitry can place the data on bus 402. Bus 402 carries the data to main memory 406, from which processor 404 retrieves and executes the instructions. The instructions received by main memory 406 may optionally be stored on storage device 410 either before or after execution by processor 404.

Computer system 400 also includes a communication interface 418 coupled to bus 402. Communication interface 418 provides a two-way data communication coupling to a network link 420 that is connected to a local network 422. For example, communication interface 418 may be an integrated-services digital network (ISDN) card, cable modem, satellite modem, or a modem to provide a data communication connection to a corresponding type of telephone line. As another example, communication interface 418 may be a local area network (LAN) card to provide a data communication connection to a compatible LAN. Wireless links may also be implemented. In any such implementation, communication interface 418 sends and receives electrical, electromagnetic or optical signals that carry digital data streams representing various types of information.

Network link 420 typically provides data communication through one or more networks to other data devices. For example, network link 420 may provide a connection through local network 422 to a host computer 424 or to data equipment operated by an Internet Service Provider (ISP) 426. ISP 426 in turn provides data communication services through the world-wide packet data communication network now commonly referred to as the "Internet" 428. Local network 422 and Internet 428 both use electrical, electromagnetic or optical signals that carry digital data streams. The signals through the various networks and the signals on network link 420 and through communication interface 418, which carry the digital data to and from computer system 400, are example forms of transmission media.

Computer system 400 can send messages and receive data, including program code, through the network(s), network link 420 and communication interface 418. In the Internet example, a server 430 might transmit a requested code for an application program through Internet 428, ISP 426, local network 422 and communication interface 418.

The received code may be executed by processor 404 as it is received, and/or stored in storage device 410, or other non-volatile storage for later execution.

3. In-Ground Sensor Systems with Modular Sensors and Wireless Connectivity Components

3.1. Overview of Example Sensor System

Figure 7:
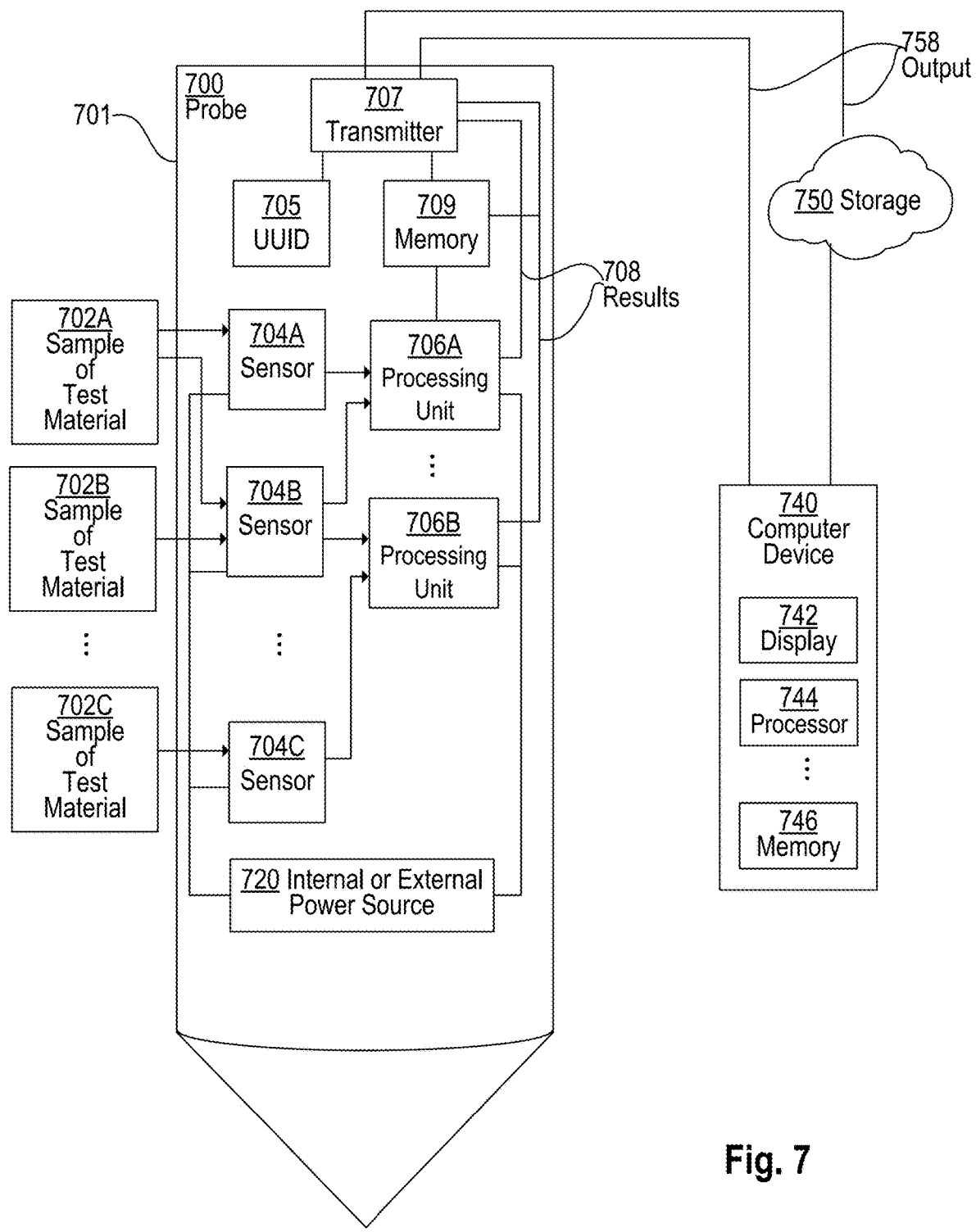
FIG. 7 depicts an example in-ground sensor system with modular sensors and wireless connectivity components that is configured to determine field properties in soil.

FIG. 7 depicts an example in-ground sensor system with modular sensors and wireless connectivity components that is configured to determine field properties in soil. In the example of FIG. 7, an in-ground integrated sensor system 701 is enclosed in a probe 700. Probe 700 includes a sealed housing that protects components of integrated sensor system 701 from moisture, dust, and other elements. In-ground integrated sensor system 701 may include one or more sensors 704A-704C, one or more processing units 706A-706B, one or more data transmitters (or transceivers) 707, and one or more internal or external power supply sources 720. Sensors 704A-704C may be configured to perform an analysis of soil samples 702A-702C, while processing units 706A-706B may use the outcomes of the analysis to generate results 708. Results 708 may be stored in memory 709 and/or provided to transmitters 707. Results 708 may be used to generate output 758.

Transmitters or transceivers 707 may be configured to establish communications connections with storage devices 750 and/or computer devices 740, and to transmit output 758 from transmitters 707 to devices 750/740. Power sources 720 may be any type of charge-providing components such as conventional batteries or solar panels that are configured to supply electrical voltage to sensors 704A-704C, processing units 706A-706B, transmitters 707, and memory 709.

Samples 702A-702C are samples of soil that may be detected by integrated sensor system 701 once the system is inserted into soil. For example, sample 702A may be a field soil sample that is detected by sensor 704A once sensor 704A is in contact with the soil.

Memory units 709 may be used to store results 708, and optionally to store a UUID of sensor system 701. The UUID of sensor system 701 may be also encoded as a QR code and imprinted on an outside wall of probe 700 as a mark 705. An example of the QR code representing a UUID of sensor system 701 is described in FIG. 9E. The UUID of sensor system 701 may be included in output 758 along with results 708. In some embodiments, each sensor 704A-704C has an associated UUID. The UUIDs may be stored in memory 709, and/or encoded as QR codes that may be imprinted on the outside wall of probe 700 as marks 705. For example, if processing unit 706A generates results 708 based on soil property measurements received from sensor 704A, then processor 706A may combine results 708 with a UUID of sensor 704A to form output 758, and transmitter 707 may transmit output 758 to devices 750/740.

3.1.1. Modular Sensors

Each of the sensors 704A-704C may include any devices configured to measure properties of soil samples 702A-702C. Sensors 704A-704C may be implemented as modules of integrated sensor system 701, and therefore, sensors 704A-704C are referred to as modular sensors. Sensors 704A-704C may include nitrate sensors, capacitive moisture sensors, resistive soil moisture sensors, time-domain reflectometry moisture sensors, and temperature sensors. Sensors 704A-704C may also include anemometers to measure the speed of the wind and rainfall sensors to measure rainfall precipitation.

In an embodiment, Sensors 704A-704C are connected to an agricultural intelligence computer system 130 and/or the agricultural apparatus 111, such as the FIELDVIEW. The data from the sensors may be sent to the FIELDVIEW for processing, and/or may be used by the FIELDVIEW to derive various recommendations/assessments for the field soils.

A nitrate sensor is an electronic chemical sensor configured to measure a concentration level of nitrate in soil. The nitrate sensor may be implemented in a silicon dioxide chip and may include silicon substrates that are placed on a printed circuit board plate. The plate may have a 10-pin female Harwin connector. The substrates, the plate, and the connector may be enclosed in a cartridge that may be covered, or coated, using epoxy or another sealer to allow only the pins of the connector protrude the cartridge. An example of nitrate sensor is described in FIG. 9A.

In some embodiments, each nitrate sensor may comprise a reference field-effect transistor (REFET) having a first element that is N-sensitive and a second element that is not N-sensitive, the two elements being packaged adjacent one another. In such an embodiment, calibration of the N-sensor may be achieved by calculating a difference in signal of the two elements, thus indicating the influence of changing N concentration. In some embodiments, a processor may execute stored programs, retrieved from a storage system, that are configured to receive millivolt response signals from sensors and convert the signals to part-per-million measurement data. Embodiments with nitrate sensors provide the capability to conduct in-field N measurements and generate recommendations for fertility treatments in the field based on wirelessly transmitting the N measurements to handheld computing devices that are programmed with recommendation programs and/or to cab computers in agricultural apparatus that are similarly programmed to generate recommendations for side dress or other applications of N in the field. In some embodiments, side dress N recommendations may use the Iowa State University PSNT-based side dress N recommendation model, implemented using program instructions in mobile computing devices that are coupled to the sensor systems. Additionally, or alternatively, program instructions may implement a recommendation engine to use soil properties obtained in real-time via the sensor system to generate rules specific for the then-current field. For example, organic matter or texture measurements can be used to derive a field-specific N threshold and conversion rate that can be transformed into a side dress rate value. For example, one programmed rule may specify that side dress rate in lbs./acre={0 if PSNT>=25 ppm for the top 1 foot of soil} OR {(25−PSNT)*8 if PSNT<25 ppm for the top 1 foot}.

A capacitive moisture sensor is an electronic device that uses capacitance to measure the dielectric permittivity of soil. The capacitive moisture sensor may include an access tube that is made of PVC and that can be installed in the soil, and a sensing head that may include an oscillator circuit, an annular electrode and fringe-effect capacitor(s) that are configured to measure the dielectric permittivity of the soil. The output of the capacitive moisture sensor includes the frequency response of the soil's capacitance due to the soil moisture level. An example of the capacitive moisture sensor is described in FIG. 9B.

A resistive soil moisture sensor is an electronic device that includes two probes which are used to measure the volumetric content of water in soil. The two probes are used to generate and measure the current that passes through the soil between the probes. As the current passes the soil, the probes measure the resistance value that can be converted to the moisture value. When the soil is moist, the soil conducts more electricity and therefore, the soil provides less resistance and the moisture level in the soil is relatively high. However, when the soil is dry, the soil conducts less electricity, and therefore, the soil provides more resistance and the moisture level in the soil is relatively low.

A time-domain reflectometry (TDR) moisture sensor is an electronic device configured to measure water content in soil. The TDR sensor implements a measurement technique that correlates the frequency-dependent electric and dielectric properties of soil to their moisture content. The technique usually involves inserting the TDR sensor into the soil and applying either a standard waveform analysis to soil samples to determine the average moisture content along the sensor or a profile analysis to measure moisture content at discrete points along the sensor. An example of the TDR sensor is described in FIG. 9C.

A temperature sensor is an electronic device configured to measure temperature of soil. The device may provide temperature measurements derived based an electrical signal. The device may include a thermocouple, also referred to as a resistance temperature detector, that includes two dissimilar metals that generate electrical voltage that is in a direct proportion to changes in temperature of the soil. Examples of the temperature sensor are described in FIGS. 9B and 9D.

In an embodiment, processing units 706A-706B are any type of computer-based processors configured to receive and process data. processing units 706A-706B are enclosed in probe 700 of integrated sensor system 701. processing units 706A-706B may be coupled to sensors 704A-704C included in probe 700 and may be configured to receive measures of soil properties from sensors 704A-704C. Some processing units 706A-706B may be part of some of sensors 704A-704C and fabricated on the same chip as sensors 704A-704C.

Processing units 706A-706B may be configured to receive data from sensors 704A-704C and process the received data. The processing may include converting data representing measures of soil properties determined by sensors 704A-704C for soil samples 702A-702C. The conversion may include determining sizes of the samples, normalizing the measures of the properties in the samples, and determining the concentration levels of the properties within a standardized range and/or using standardized units. For example, a nitrate concentration level in sample 702A may be expressed as a count of nitrate parts per million in a standardized size of sample 702A. Once processing units 706A-706B determine the concentration levels of the properties in the samples, the processors may provide results 708 to transmitter 707 and/or store results 708 in memory 709.

Results 708 may be stored locally in memory 709 and/or in a removable storage device (not depicted in FIG. 7) such as a secure digital ("SD") card. An SD card is a non-volatile flash memory card for use in portable devices.

In an embodiment, transmitters or transceivers 707 transmit results 708 directly to an LTE modem (not depicted in FIG. 7) or a long range (LoRA) radio arrangement (not depicted in FIG. 7). The LoRA is a digital wireless data communication technology developed to utilize radio frequency bands to communicate data. The LoRA uses sub-gigahertz radio frequency bands like 169 MHz, 433 MHz, 868 MHz and 915 MHz to enable very-long-range transmissions of data with low power consumption.

In-ground integrated sensor system 701 may include transmitters, transceivers or both. The transmitters and transceivers are electronic devices that are configured to establish communications connections with computer devices and transmit electronic data to the computer devices via the established connections. The difference between a transmitter and a transceiver is that the transmitter is not configured to receive data from other devices while the transceiver is configured to handle bi-directional communications with other devices.

If in-ground integrated sensor system 701 includes at least one transmitter 707, then the transmitter may transmit output data 758 as soon as results 708 are provided to transmitter 707. In this configuration, integrated sensor system 701 may operate in a data push-mode as transmitter 707 transmits, or pushes, output data 758 out as soon as results 708 are available.

If in-ground integrated sensor system 701 includes at least one transceiver, then integrated sensor system 701 may be queried by another device for providing output data 758. In this configuration, integrated system 701 may operate in a data pull-mode as the transceiver may provide output 758 upon receiving requests for output data 758. In this configuration, integrated system 701 may also operate in a data push-mode as the transceiver may transmit output data 758 even if no request for output data 758 is received by the transceiver.

In an embodiment, output data 758 is transmitted from probe 700 to a nearby LTE-connected hub (not depicted in FIG. 7) in compliance with the Bluetooth communications protocol, and then from the hub to devices 740/750. An example of the hub is a smart hub that is a wireless device that uses a wireless phone line and the Internet access to facilitate connections to the 4G global LTE network via Wi-Fi, LAN and/or a voice connection. The smart hub can provide wireless connectivity between transmitter 707 and devices 740/750.

In an embodiment, output data 758 is transmitted from probe 700 directly to an LTE modem (not depicted in FIG. 7) or a LoRA ratio arrangement (not depicted in FIG. 7). If output data 758 is transmitted to a LoRA-enabled device, then output data 758 is encoded into signals within a certain radio frequency band, and the encoded data is communicated to the LoRA-enabled device.

Installation of probe 700 usually includes integrating sensors 704A-704C, processing units 706A-706B, memory units 709 and other components in probe 700. Once all components are integrated in probe 700, one or more batteries may be installed in probe 700. If probe 700 uses solar panels, then a photovoltaic solar panel, or panels, may be installed on probe 700. The photovoltaic solar panel is usually included in a photovoltaic module comprising photovoltaic solar cells that absorb sunlight as a source of energy to generate electricity.

Probe 700 of in-ground sensor system 701 may be installed in soil using many approaches. According to one approach, probe 700 is inserted into a cavity created in the soil using a drill with an auger or using a spade or a shovel.

Once probe 700 is inserted into the cavity in the soil, the position and location of probe 700 may be adjusted or refined. For example, a depth of probe 700 may be adjusted until all sensors installed on probe 700 are fully covered by the soil. Once probe 700 is inserted into the cavity and power is provided to probe 700, in-ground sensor system 701 included in probe 700 may start generating soil property data.

Output data 758 may include results 708 containing soil property data determined for samples 702A-702C. Output data 758 may be provided to computer device 740 and displayed on a display 742 of computer device 740, Output data 758 may be stored in memory 744 or processed by a processor 744 of computer device 740. Examples of computer devices 740 include laptops, personal computers, mobile devices, smartphones, tablets, and the like.

In some embodiments, output data 758 is transmitted to storage system 750, and used to build a database of information about agricultural fields, and to build a data bank of agricultural data that can be used by researchers, crop growers, and agricultural industries. Output data 758 may be further analyzed and used to generate recommendations for users.

In some embodiments, output data 758 may include additional data such a UUID of integrated sensor system 701. Upon receiving output data 758, devices 740/750 may use output data 758 to create soil property maps for the field to indicate, for example, concentration levels of nitrate, phosphorus and moisture for the field. Based on the maps, devices 740/750 may generate agricultural recommendations for the field. The recommendations may be transmitted to a central server, a user computer, or directly to a computer-based controller that controls agricultural equipment.

3.2. Process Overview

Figure 8:
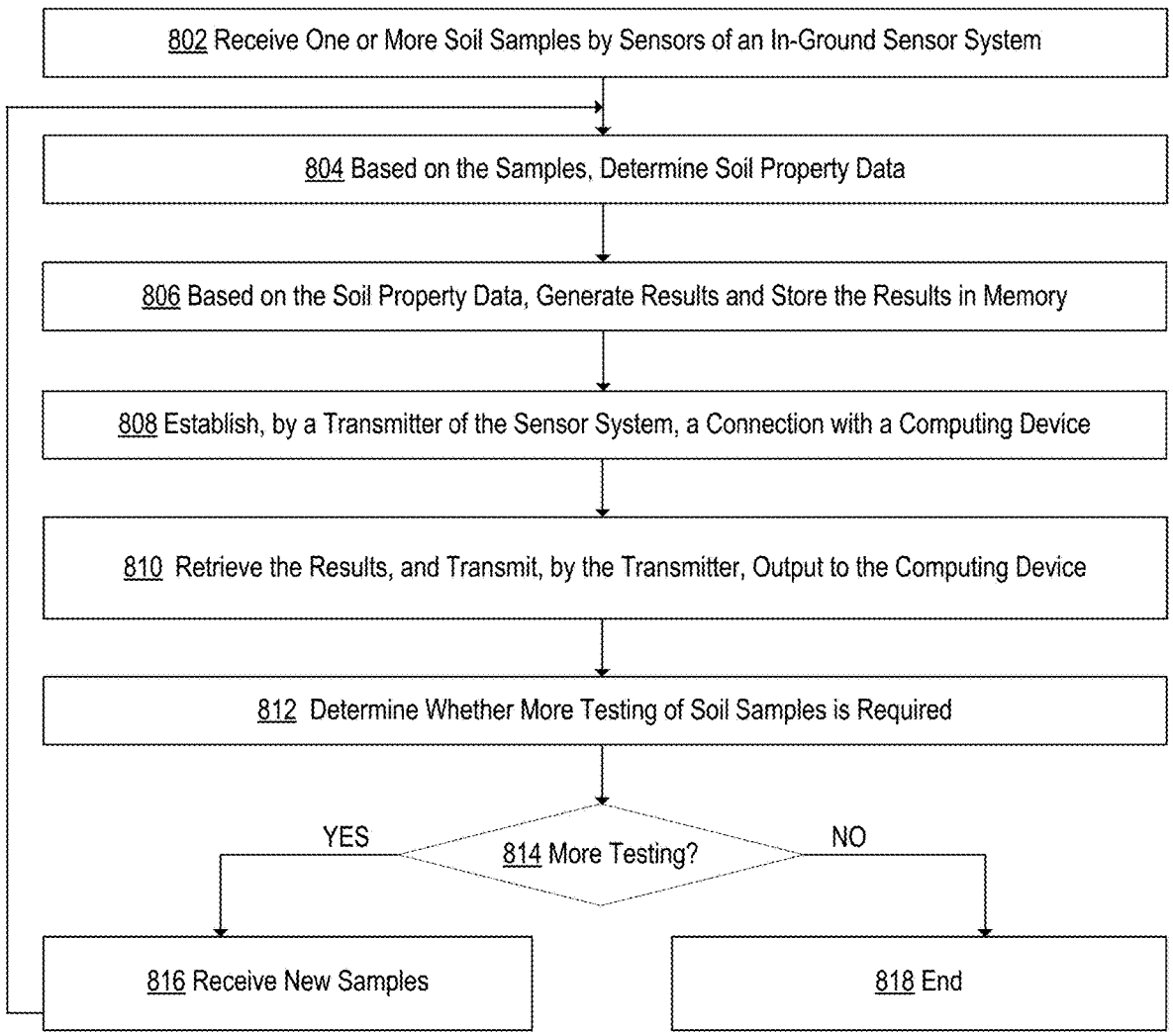
FIG. 8 depicts an example process that uses an in-ground sensor system with modular sensors and wireless connectivity components that is configured to determine field properties in soil.

FIG. 8 depicts an example process that uses an in-ground sensor system with modular sensors and wireless connectivity components that is configured to determine field properties in soil. The example process may be executed by components of in-ground sensor system 701, described in FIG. 7, but other embodiments of FIG. 8 may interoperate with other kinds of systems. The process depicted in FIG. 8 may be executed on a continuous basis, according to a programmed schedule, or in response to receiving a trigger from an operator or a user. The trigger may be generated when the user generates a message or instructions and transmits them wirelessly to the sensors.

In step 802, a sensor system receives one or more soil samples. For example, sensor system may receive the samples when any of sensors 704A-704C, depicted in FIG. 7, are in contact with the soil. For example, if probe 700 is inserted into the soil, then sensors 704A-704C may touch the soil, and thus receive the soil samples.

In step 804, the sensor system determines soil property data in soil samples. This may include measuring, using sensors 704A-704C, one or more soil properties in the soil samples, and then computing, using processing units 706A-706B, the soil property data based on the measures. Depending on the specification of sensors 704A-704C, the soil property data may include levels of concentration of nitrate, phosphorus, chlorine, pH, potassium, or other elements present in the samples.

In step 806, the sensor system uses the soil property data to generate results 708. Results 708 may include the soil property data and, optionally, a UUID of in-ground sensor system 701, or UUIDs of sensors 704A-704C. processing units 706A-706B may retrieve the UUIDs from a memory chip of the in-ground sensor system and combine the soil property data with the retrieved UUIDs to form results 708. Results 708 may be stored in memory cache or memory unit 709 of the sensor system.

In step 808, the sensor system establishes a communications connection with storage device 750, computer device 740 or a smart hub (not depicted in FIG. 7) that may be used as a proxy for storage device 750 and/or computer device 740. The communications connection may be established by transmitter 707 of in-ground sensor system 701. The communications connection may be a wireless Wi-Fi-based communications connection, or a wire-based LAN or WAN connection. Communications may be established automatically to provide autonomous reporting of soil sensor result data to other systems, or according to a schedule or in response to a triggering signal.

Once the communications connection with storage device 750, computer device 740, or the hub is established, transmitter 707, in step 810, retrieves results 708 from memory unit 709, and uses results 708 to generate output 758. In an embodiment, output 758 includes results 708 and UUID data of in-ground sensor system 701. Once output 758 is generated, transmitter 707 transmits output 758 to devices 750/740 or the hub. For example, output 758 may be transmitted to a data repository maintained by a research laboratory server or to a mobile device owned by a crop grower.

Output 758 may be provided to computer servers and/or user computers to be used to improve and enhance agricultural practices, such as fertilizing, seeding, or harvesting. For example, output 758 may be used to generate or modify agricultural prescriptions for the field. If output 758 includes, for example, information about a nitrate concentration level in a field, then output 758 may be used to determine, or adjust, an amount of the nitrogen-based fertilizer to be applied to the field to compensate for the nitrate leaching occurred over time.

Output 758 may be transmitted to a computer-based controller that controls agricultural equipment such as seeders and planters. For example, output 758 that includes information indicating some ponding water in a field plot may be transmitted to a computer-based controller of a seeder and used by the controller to instruct the seeder to avoid dispensing the seeds in the plot covered with water.

In step 812, the sensor system tests whether more testing of the test material or other materials is required. If, in step 814, the sensor system determines that more testing is required, then the sensor system proceeds to performing step 816, in which the sensor system receives one or more new soil samples and proceeds to performing step 804. However, if no more testing is required at this time, then, in step 818, the sensor system stops executing.

4. Example Implementations 4.1. Handheld Integrated Sensor Systems

Figure 9A:
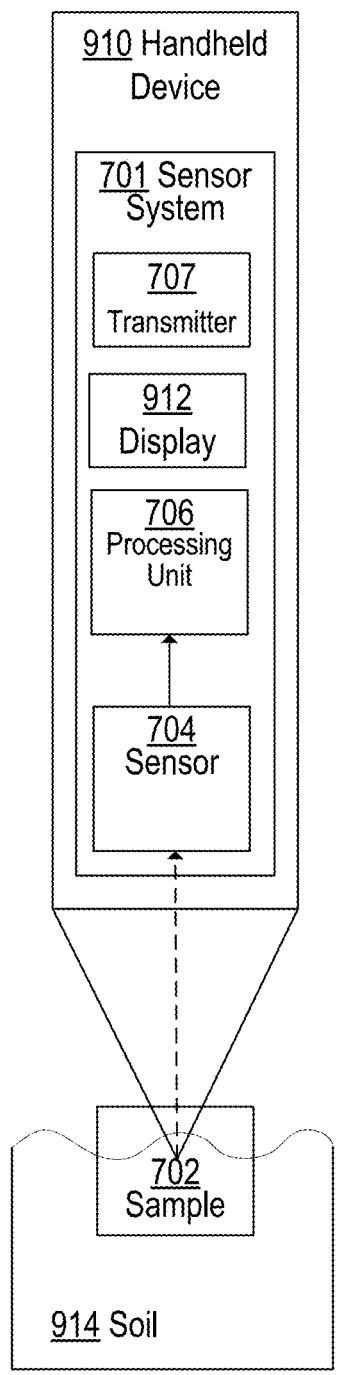
FIG. 9A depicts an example in-ground sensor system implemented in a handheld device and comprising modular sensors, processors, and wireless connectivity components.

FIG. 9A depicts an example in-ground sensor system implemented in a handheld device and comprising modular sensors, processors, and wireless connectivity components. In the depicted example, a handheld device 910 includes an in-ground sensors system 701. Handheld device 910 may be a portable device that is convenient to carry and use in the field. Handheld device 910 may be shaped as an elongated probe that has a shaft portion used to host in-ground sensor system 701 and a pin portion used to insert handheld device 910 into soil.

In an embodiment, handheld device 910 comprises one or more sensors 704, one or more processing units 706, and one or more internal or external power sources (not depicted in FIG. 9A).

In some embodiments, handheld device 910 includes a display 912 that may be configured to display output data calculated by processing units 706. Handheld device 910 may also include a transmitter (or a transceiver) 707 configured to establish communications connections between handheld device 910 and other computer systems, such as storage systems or computer devices (not depicted in FIG. 9A) to facilitate data exchange with other systems.

Handheld device 910 may be used to calculate soil property data for field soils. Once handheld device 910 is inserted into a cavity created in soil, handheld device 910 becomes in contact with soil samples 702. Upon detecting soil samples 702, in-ground sensor system 701 performs an analysis of content of soil samples 702. Results of the analysis may include information about a concentration level of nitrate or other elements in the soil. The results may be displayed on display 912, which may be equipped with any type of interface, including a graphical user interface.

If handheld device 910 is equipped with transmitter (or a transceiver) 707, then transmitter 707 may electronically transmit the results to other computer systems (not depicted in FIG. 9A).

In an embodiment, in-ground sensor system 701 is implemented in an integrated circuit that may be enclosed in a sealed cartridge and integrated with handheld device 910. Because the cartridge-based sensor system is portable, sensor system 701 may be used to measure nutrient concentration levels at any location and at any time, and thus overcomes the shortcomings of the conventional systems that require sending the soil samples to laboratories and receiving the results on a delayed basis.

4.2. Blade-Based Integrated Sensor Systems

Figure 9B:
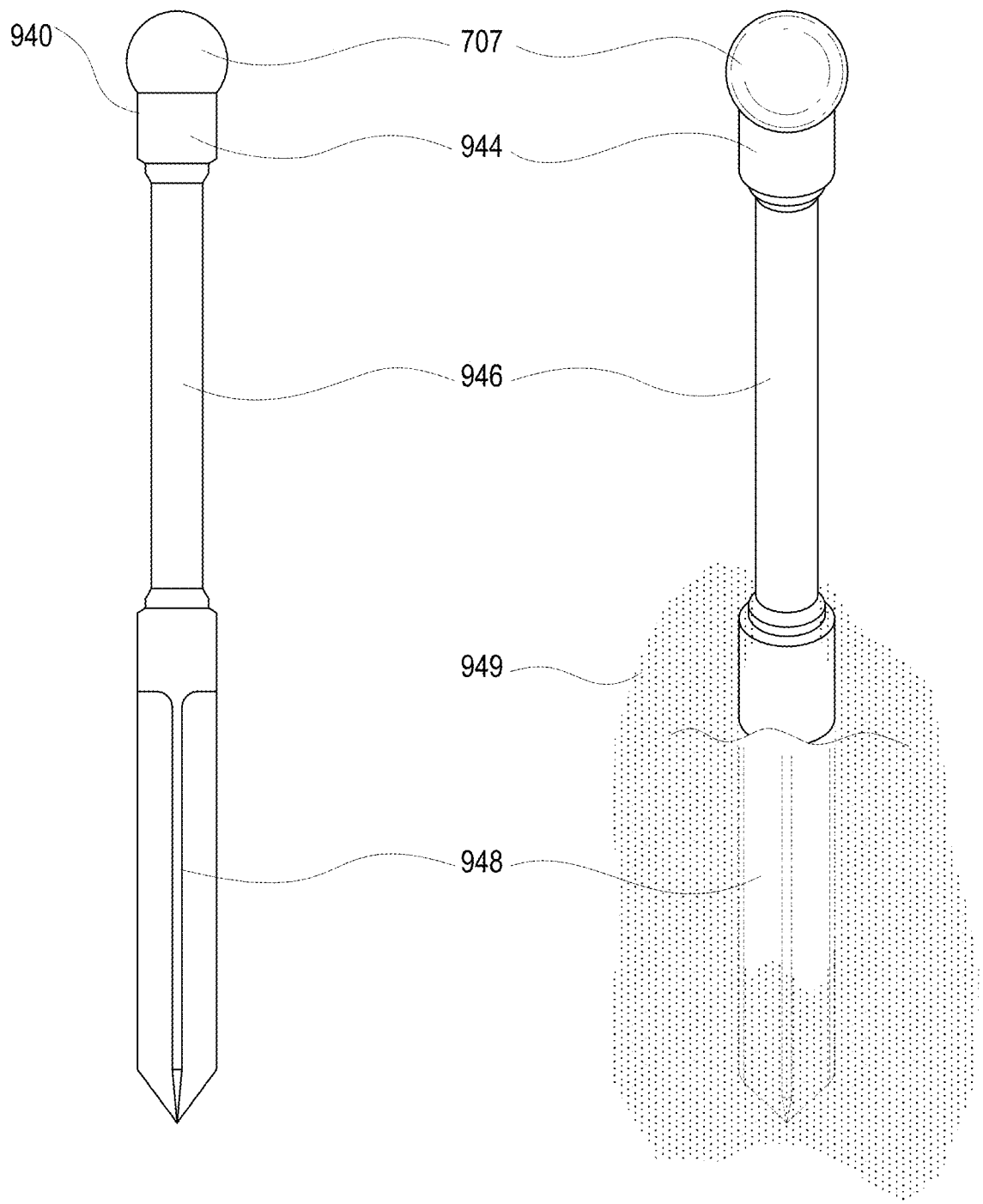
FIG. 9B depicts two views of an example in-ground moisture and temperature sensor system implemented in an in-ground blade and comprising modular sensors, processors, and wireless connectivity components.

FIG. 9B depicts two views of an example in-ground moisture and temperature sensor system implemented in an in-ground blade and comprising modular sensors, processors, and wireless connectivity components. The view on the left side is a front view of an example in-ground blade 940, while the view on the right side is a perspective view of example in-ground blade 940.

In the depicted example, in-ground blade 940 includes a transmitter 707, a connector 944, a shaft 946 for storing a temperature sensor and a capacitive moisture sensor, and a blade 948 for inserting in-ground blade 940 into soil 949. In some embodiments, in-ground blade 940 includes additional sensors (not depicted in FIG. 9B) such as time-domain reflectometry moisture sensors or resistive soil moisture sensors.

A temperature sensor is an electronic device configured to measure temperature of soil 949. The temperature sensor may include an RTD that includes two dissimilar metals that generate electrical voltage in direct proportion to changes in temperature of the soil. The temperature sensor may measure the RTD changes in the voltage to determine the changes in the temperature of soil 949.

A capacitive moisture sensor is an electronic device that uses capacitance to measure the dielectric permittivity of soil 949. The capacitive moisture sensor may include an access tube that can be installed in the soil, and a sensing head that may include an oscillator circuit, an annular electrode and fringe-effect capacitors configured to measure the dielectric permittivity of soil 949.

In-ground blade 940 may be either permanently or adjustably inserted into soil 949. The adjustability provides many benefits since the properties of soil are not homogeneous throughout the soil. For example, the properties of the soil at the soil depth of 6 inches may be different than the properties of the soil at the soil depth of 12 inches.

In an embodiment, a plurality of in-ground blades 940 is used to determine and compute soil property data for various locations throughout a field. A crop grower may use the plurality of in-ground blades 940 to collect soil property data for various plots of the field and use the collected information to efficiently manage the field. For example, the grower may use the received soil property data to vary the amounts of fertilizer used in the plots, and to adjust the fertilization schedules depending on the current levels of nutrients in the plots.

Figure 9C:
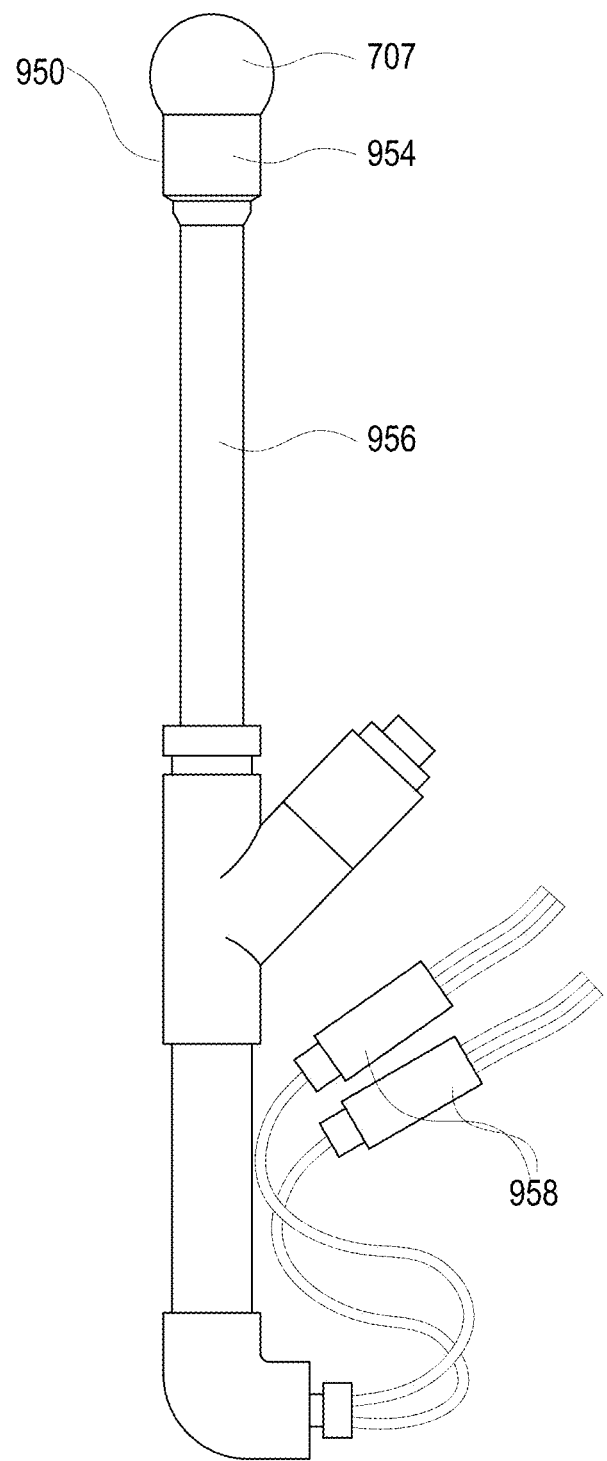
FIG. 9C depicts an example in-ground sensor system comprising modular sensors, processors, and wireless connectivity components.

FIG. 9C depicts an example in-ground sensor system comprising modular sensors, processors, and wireless connectivity components. In the depicted example, an in-ground sensor system 950 includes a transmitter 707, a connector 954, a shaft 956 for storing, for example, a TDR sensor, and two rods 958 that can be inserted into soil. In some embodiments, in-ground sensor system 950 includes additional sensors (not depicted in FIG. 9B) such as capacitive moisture sensors, nitrate sensors, or resistive soil moisture sensors. A TDR sensor is an electronic device configured to measure moisture content in soil. The TDR includes parallel rods 958 that act as transmission lines. A voltage is applied to the rods and is reflected to the TDR sensor for analysis. The speed or velocity of the voltage pulse measured along the rods is related to the dielectric permittivity of the soil.

Figure 9D:
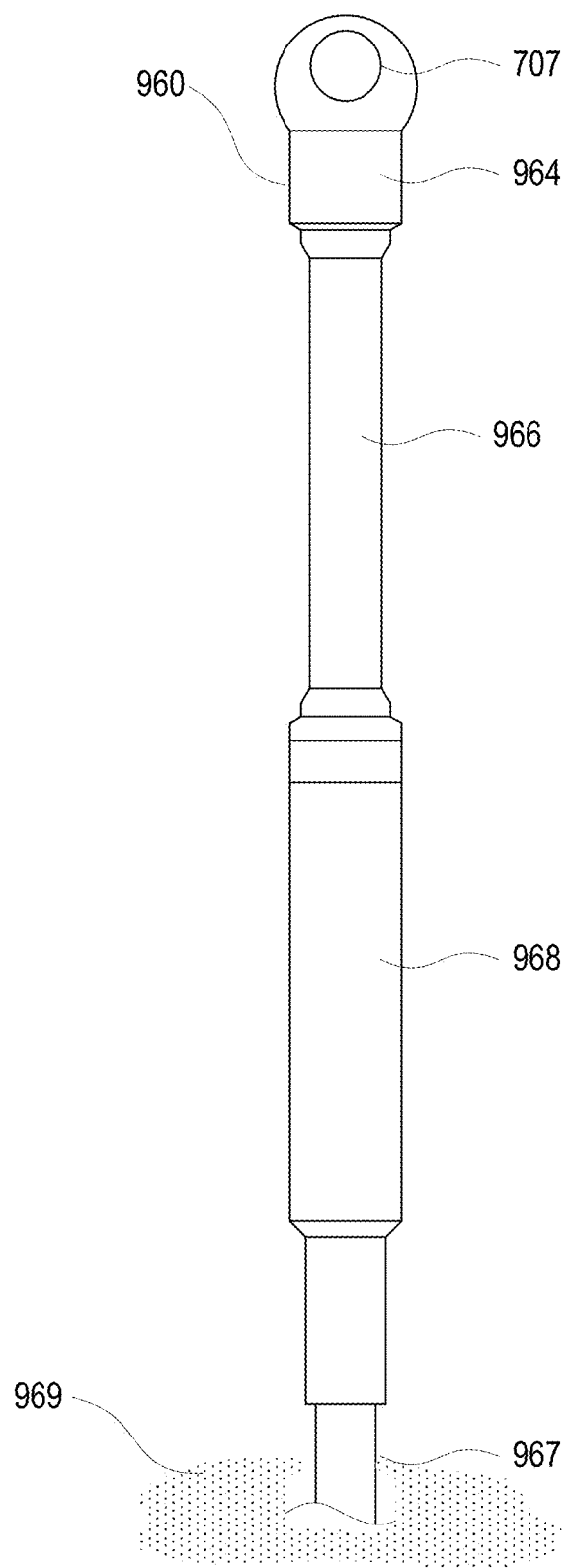
FIG. 9D depicts an example in-ground nitrate, moisture, and temperature sensor system implemented in an in-ground blade and comprising modular sensors, processors, and wireless connectivity components.

FIG. 9D depicts an example in-ground nitrate, moisture, and temperature sensor system implemented in an in-ground blade and comprising modular sensors, processors, and wireless connectivity components. In the depicted example, an in-ground sensor system 960 includes transmitter 707, a connector 964, shafts 966-968 for storing a nitrate sensor, a TDR sensor, a capacity moisture sensor, and a temperature sensor, and a blade 967 that can be inserted into soil 969. In some embodiments, in-ground sensor system 960 includes additional sensors (not depicted in FIG. 9B). The nitrate sensor, the TDR sensor, the capacity moisture sensor and the temperature sensors are described above.

Figure 9E:
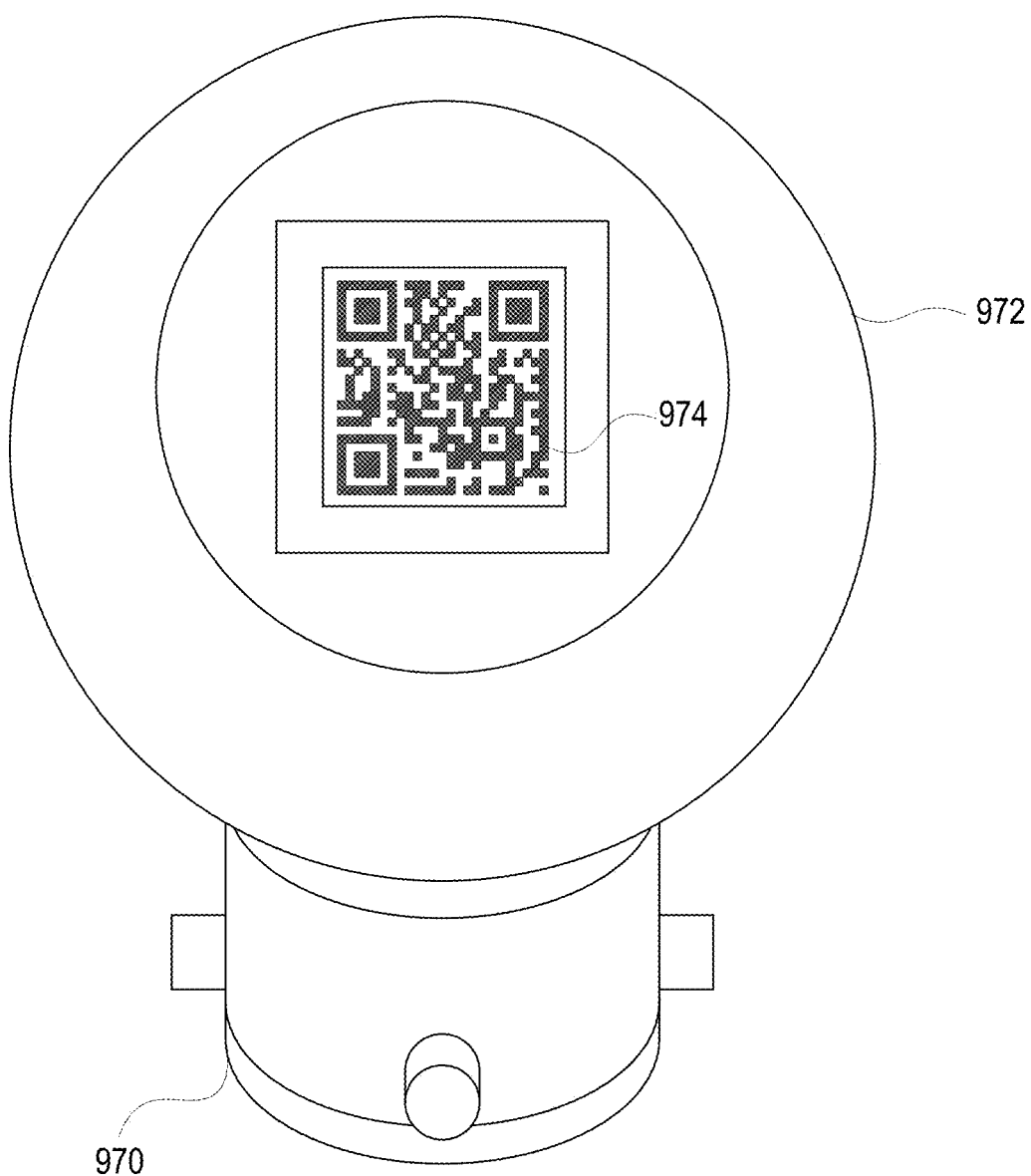
FIG. 9E depicts an example in-ground sensor system that includes a system identifier.

FIG. 9E depicts an example in-ground sensor system that includes a system identifier. In the depicted example, an in-ground sensor system 970 includes an identifier 974. Identifier 974 includes a QR code that encodes, for example, a UUID of in-ground sensor system 970. Identifier 974 may be a laminated piece of paper that has the QR code imprinted on it. Identifier 974 may be attached to a top portion 972 of in-ground sensor system 970.

Figure 9F:
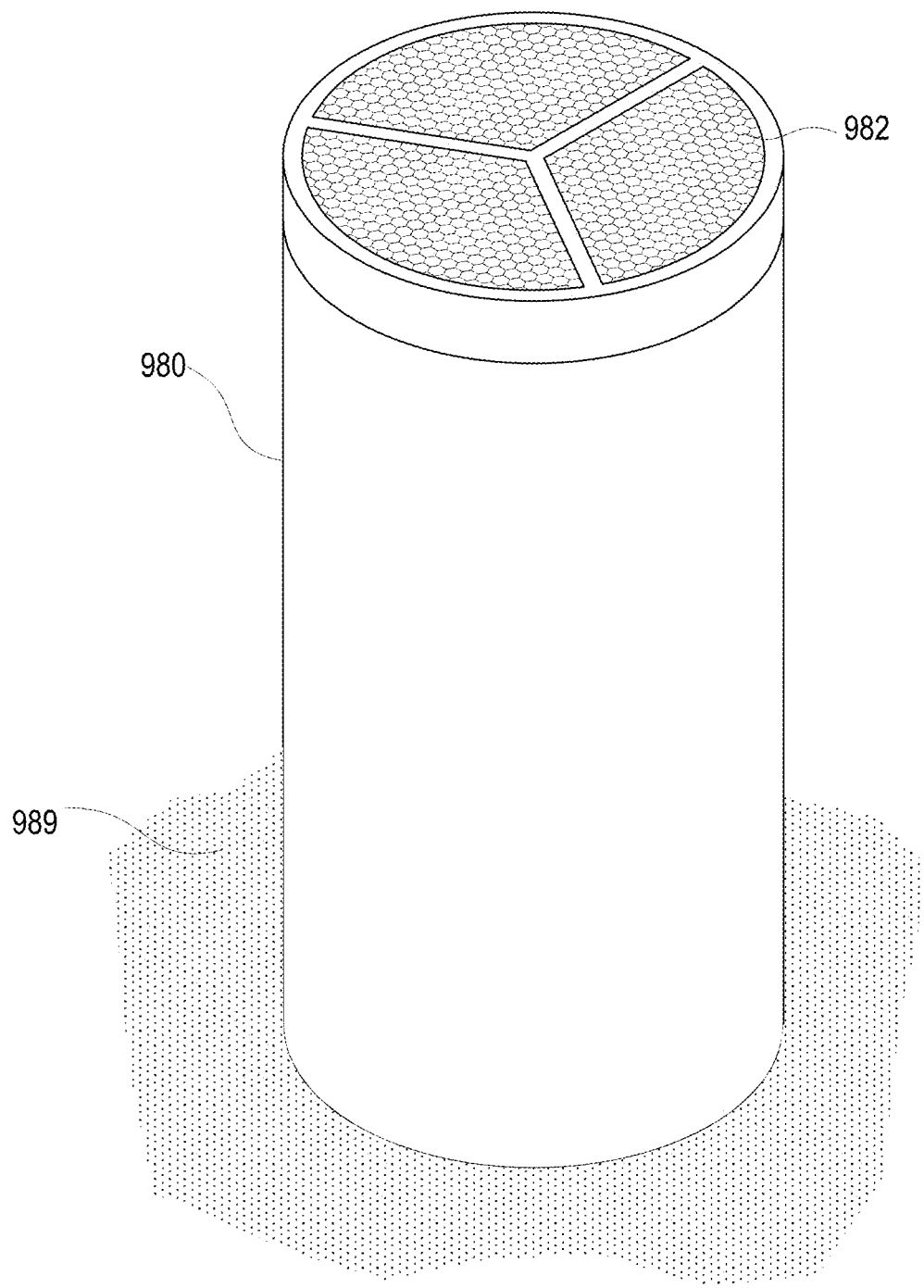
FIG. 9F depicts an example in-ground sensor system that includes a transceiver.

FIG. 9F depicts an example in-ground sensor system that includes a transmitter. In the depicted example, an in-ground sensor system 980 includes, in addition to sensors, processors, and power supply (not depicted in FIG. 9F), a transmitter 982. Transmitter 982 may be installed in an upper part of in-ground sensor system 980, or at least above a lower part of in-ground sensor system 980 that is usually submerged in soil 989. In some embodiments, transmitter 982 may be implemented as a transceiver that is configured to not only establish communications connections with other devices and transmit data to the devices, but also to receive electronic data from the devices.

5. Extensions and Alternatives

In the foregoing specification, embodiments have been described with reference to numerous specific details that may vary from implementation to implementation. The specification and drawings are, accordingly, to be regarded in an illustrative rather than a restrictive sense. The sole and exclusive indicator of the scope of the disclosure, and what is intended by the applicants to be the scope of the disclosure, is the literal and equivalent scope of the set of claims that issue from this application, in the specific form in which such claims issue, including any subsequent correction.

6. Improvements Provided by Certain Embodiments

In an embodiment, an in-ground sensor system with a plurality of different integrated modular sensors and wireless connectivity components provides an improved, multi-component system for monitoring multiple different properties of field soils and wirelessly transmitting soil property data to other devices. The in-ground sensor system may be configured and programmed to determine the soil property data on contact with soil samples and the soil property data may be automatically and wirelessly transmitted from the in-ground sensor system to other devices. The versatility and convenience of the in-ground sensor system allow overcoming the shortcomings of conventional systems that require sending soil samples to laboratories and awaiting the results for some time. Therefore, embodiments can provide in-season soil measurements with little delay between the time of sampling and the time of evaluation of the sample. Consequently, growers obtain better, near real-time data on soil properties of fields.

Embodiments may provide the benefits of convenient and accurate monitoring nutrient concentration in soil over time. For example, since an in-ground sensor system allows monitoring the nutrient concentration in the soil at any time and as frequently as needed, the system allows tracking the changes in the nutrient concentration in the soil accurately and precisely. Embodiments may provide the benefits of helping farmers and researchers to monitor properties of field soils to improve agricultural practices. Soil property data provided for a field by an in-ground sensor may be used to determine, for example, optimized amounts of fertilizers for the field and optimized schedules for applying the fertilizers to the field.

Furthermore, embodiments may be packaged to provide easy installation in fields, reliable operation over multiple growth seasons, and autonomous reporting of data.

What is claimed is:

1. An integrated sensor system comprising:
   one or more sensors, installed in an in-ground blade, that are configured to determine one or more measures of at least one property of soil;
   one or more processing units, installed in the in-ground blade, that are configured to receive, from the one or more sensors, the one or more measures of at least one property of soil, and calculate soil property data based on the one or more measures of at least one property of soil; and
   a transmitter, installed in an in-ground blade, that is configured to receive the soil property data from the one or more processing units, establish a communications connection with at least one computer device, and automatically transmit, via the communications connection, the soil property data to the at least one computer device configured on at least one agricultural machine.

2. The integrated sensor system of claim 1, wherein the at least one computer device uses the soil property data to control the at least one agricultural machine as the at least one agricultural machine performs agricultural tasks in an agricultural field;
wherein the transmitter is configured to establish a wireless communications connection with the at least one computer device; wherein the wireless communications connection is configured to communicate data in compliance with any type of wireless communications protocol including a Bluetooth communications protocol.

3. The integrated sensor system of claim 1, further comprising:
a probe configured to provide a housing for the one or more sensors, the one or more processing units, and the transmitter;
a power supply source configured to supply power to components of the integrated sensor system; wherein the power supply source includes one or more of: a battery, or a solar panel;
one or more imaging sensors;
one or more anemometers; and
one or more rainfall sensors.

4. The integrated sensor system of claim 3, wherein the probe is installed in a cavity created in soil; wherein the probe is powered up once the power supply source is provided; wherein the probe is initiated once a probing depth is set.

5. The integrated sensor system of claim 3, wherein the probe is installed in the in-ground blade.

6. The integrated sensor system of claim 1, wherein the soil property data comprises information about one or more time-sensitive soil properties; wherein the soil property data is transmitted to a storage device and used to generate a database repository of information about soil; wherein the soil property data is transmitted to a computer system to generate one or more agricultural prescriptions for a field; wherein the one or more agricultural prescriptions are provided to one or more user devices configured to control agricultural equipment.

7. The integrated sensor system of claim 1, wherein the soil property data is transmitted to a cloud-based storage system for storage; wherein the soil property data transmitted to the cloud-based storage system is associated with one or more of: date information indicating a date on which the one or more measures of at least one property of soil were determined, a location, one or more universal unique identifiers ("UUIDs"), or weather information.

8. The integrated sensor system of claim 1, wherein the soil property data includes one or more of: a phosphorus concentration level, a nitrate concentration level, a potassium concentration level, a moisture level, a rainfall level, a pH level, or a chlorine level.

9. The integrated sensor system of claim 1, wherein the one or more sensors include one or more: a capacitive moisture sensor, a time-domain reflectometry moisture sensor, a temperature sensor, or a nitrate sensor.

10. A computer-implemented method for monitoring properties of field soil using an integrated sensor system, the method comprising:
determining, using one or more sensors, installed in an in-ground blade of an integrated sensor system, one or more measures of at least one property of soil;
receiving, by one or more processing units, installed in the in-ground blade of the integrated sensor system, the one or more measures of at least one property of soil from the one or more sensors;
calculate, by the one or more processing units, soil property data based on the one or more measures of at least one property of soil;
receiving, by a transmitter, installed in the in-ground blade of the integrated sensor system, the soil property data from the one or more processing units;
establishing, by the transmitter, a communications connection with at least one computer device; and
automatically transmitting, by the transmitter, the soil property data via the communications connection to the at least one computer device configured on at least one agricultural machine.

11. The computer-implemented method of claim 10, wherein the at least one computer device uses the soil property data to control the at least one agricultural machine as the at least one agricultural machine performs agricultural tasks in an agricultural field;
wherein the transmitter is configured to establish a wireless communications connection with the at least one computer device; wherein the wireless communications connection is configured to communicate data in compliance with any type of wireless communications protocol including a Bluetooth communications protocol.

12. The computer-implemented method of claim 10, wherein the one or more sensors, the one or more processing units, and the transmitter are housed in a probe of the integrated sensor system; wherein the probe protects components installed inside the probe from moisture, dust, and other elements; wherein power is supplied to components of the integrated sensor system by a power supply source which includes one or more of: a battery, or a solar panel; wherein the integrated sensor system further comprises one or more of: an imaging sensor, an anemometer, or a rainfall sensor.

13. The computer-implemented method of claim 12, wherein the probe is installed in a cavity created in soil; wherein the probe is powered up once the power supply source is provided; wherein the probe is initiated once a probing depth is set.

14. The computer-implemented method of claim 12, wherein the probe is installed in the in-ground blade.

15. The computer-implemented method of claim 10, wherein the soil property data comprises information about one or more time-sensitive soil properties; wherein the soil property data is transmitted to a storage device and used to generate a database repository of information about soil; wherein the soil property data is transmitted to a computer system to generate one or more agricultural prescriptions for a field; wherein the one or more agricultural prescriptions are provided to one or more user devices configured to control agricultural equipment.

16. The computer-implemented method of claim 10, wherein the soil property data is transmitted to a cloud-based storage system for storage; wherein the soil property data transmitted to the cloud-based storage system is associated with one or more of: date information indicating a date on which the one or more measures of at least one property of soil were determined, a location, one or more universal unique identifiers ("UUIDs"), or weather information.

17. The computer-implemented method of claim 10, wherein the soil property data includes one or more of: a phosphorus concentration level, a nitrate concentration level, a potassium concentration level, a moisture level, a pH level, a rainfall level, or a chlorine level.

18. The computer-implemented method of claim 10, wherein the one or more sensors include one or more: a capacitive moisture sensor, a time-domain reflectometry moisture sensor, a temperature sensor, or a nitrate sensor.

* * * * *